US012778470B2

(12) United States Patent
Kutsuna et al.

(10) Patent No.: US 12,778,470 B2
(45) Date of Patent: Nov. 3, 2026

(54) SENSOR AND MANUFACTURING METHOD THEREFOR

(71) Applicant: PHC Holdings Corporation, Tokyo (JP)

(72) Inventors: Fuminori Kutsuna, Ehime (JP); Masaki Fujiwara, Ehime (JP); Masami Tomioka, Ehime (JP); Toshihiro Ikeda, Ehime (JP); Masatomo Matsui, Ehime (JP); Makoto Sueyoshi, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 1115 days.

(21) Appl. No.: 17/800,100

(22) PCT Filed: Feb. 26, 2021

(86) PCT No.: PCT/JP2021/007534
§ 371 (c)(1),
(2) Date: Aug. 16, 2022

(87) PCT Pub. No.: WO2021/172564
PCT Pub. Date: Sep. 2, 2021

(65) Prior Publication Data

US 2023/0105478 A1 Apr. 6, 2023

Related U.S. Application Data

(60) Provisional application No. 62/983,013, filed on Feb. 28, 2020.

(51) Int. Cl.

| | |
|---|---|
| ***A61B 5/1486*** | (2006.01) |
| ***A61B 5/00*** | (2006.01) |
| ***A61B 5/145*** | (2006.01) |

(52) U.S. Cl.
CPC ...... *A61B 5/14865* (2013.01); *A61B 5/14532* (2013.01); *A61B 5/6847* (2013.01); *A61B 5/0002* (2013.01); *A61B 2562/125* (2013.01)

(58) Field of Classification Search
CPC ............ A61B 5/14865; A61B 5/14532; A61B 5/6847; A61B 5/0002; A61B 2562/125; A61B 5/1486
See application file for complete search history.

(56) References Cited

U.S. PATENT DOCUMENTS

2010/0230285 A1 9/2010 Hoss et al.
2017/0188916 A1* 7/2017 Wang .................... C12Q 1/006
2019/0133638 A1 5/2019 Ii et al.

FOREIGN PATENT DOCUMENTS

EP 0 247 850 4/1993
EP 0 442 969 2/2002
(Continued)

OTHER PUBLICATIONS

International Search Report issued Mar. 30, 2021 in International Application No. PCT/JP2021/007534.
(Continued)

*Primary Examiner* — Navin Natnithithadha
(74) *Attorney, Agent, or Firm* — Wenderoth, Lind & Ponack, L.L.P.

(57) ABSTRACT

This sensor has a probe inserted into a living body, and measures an analyte, wherein the probe has a substrate, an electrode formed on the substrate, a reagent layer formed on the electrode, a first protective film formed on the reagent layer, and a second protective film which is thinner than the first protective film and formed on the first protective film.

12 Claims, 22 Drawing Sheets

(56) References Cited

FOREIGN PATENT DOCUMENTS

| | | |
|---|---|---|
| EP | 1 235 068 | 1/2006 |
| EP | 1 504 252 | 6/2016 |
| EP | 3 415 086 | 12/2018 |
| JP | 2012-519038 | 8/2012 |
| WO | 2017/187943 | 11/2017 |

OTHER PUBLICATIONS

Extended European Search Report issued Feb. 29, 2024 in European Patent Application No. 21761274.6.

* cited by examiner (PROCESS F)

(PROCESS G)

(PROCESS H)

(PROCESS I)

(PROCESS J)

(PROCESS F)

(PROCESS G)

(PROCESS H)

SENSOR AND MANUFACTURING METHOD THEREFOR

TECHNICAL FIELD

The present disclosure relates to a sensor and a method for manufacturing the same.

BACKGROUND ART

Embedded electrochemical glucose sensors that continuously or semi-continuously measure glucose concentrations in living bodies have been developed (see PTL 1, for example). Examples of such glucose sensors include a continuous glucose monitoring (CGM) sensor. The CGM sensor includes a bioprotective film that covers a reagent layer containing oxidoreductase and the like.

CITATION LIST

Patent Literature

PTL 1
Japanese Unexamined Patent Application Publication (Translation of PCT Application) No. 2012-519038

SUMMARY OF INVENTION

Technical Problem

If thicknesses of protective films differ from sensor to sensor, performance of the sensors vary. There is thus a need for sensors that can be easily manufactured and have reduced variations in performance.

Non-limiting examples of the present disclosure provide a sensor on which a protective film can be easily formed and which has reduced variations in performance and a method for manufacturing the same.

Solution to Problem

A sensor according to an example of the present disclosure is a sensor that measures an analyte including: a probe that is to be inserted into a living body, the probe including a substrate, an electrode that is formed on or above the substrate, a reagent layer that is formed on or above the electrode, a first protective film that is formed on or above the reagent layer, and a second protective film that is thinner than the first protective film and is formed on or above the first protective film.

A method for manufacturing a sensor according to an example of the present disclosure is a method for manufacturing a sensor that includes a probe to be inserted into a living body and measures an analyte, the method including: manufacturing the probe by forming an electrode on or above a sheet-shaped substrate; forming a reagent layer on or above the electrode; forming a first protective film on or above the reagent layer; cutting the sheet-shaped substrate into a shape of the probe; and immersing the substrate into a protective film solution and thereby forming a second protective film that is thinner than the first protective film on or above the first protective film.

Advantageous Effects of Invention

According to an example of the present disclosure, it is possible to easily manufacture a sensor and reduce variations in performance.

Further advantages and effects of the example of the present disclosure will become obvious from the specification and the accompanying drawings. Although each of such advantages and/or effects will be provided by some embodiments and features described in the specification and the accompanying drawings, it is not necessary that all the advantages and/or the effects be provided to obtain one or more same features.

DESCRIPTION OF EMBODIMENTS

Hereinafter, embodiments of the present disclosure will be described in detail with reference to the accompanying drawings as needed. However, there may also be a case in which unnecessarily detailed description is omitted. For example, there may be a case in which detailed description of matters that have already been known well and repeated description of substantially the same configurations are omitted. This is for avoiding the following description from becoming unnecessarily redundant and for facilitating understanding of those skilled in the art.

Note that the accompanying drawings and the following description are provided to allow those skilled in the art to sufficiently understand the present disclosure and are not intended to thereby limit the subject matter described in the claims.

Embodiment 1

Figure 1:
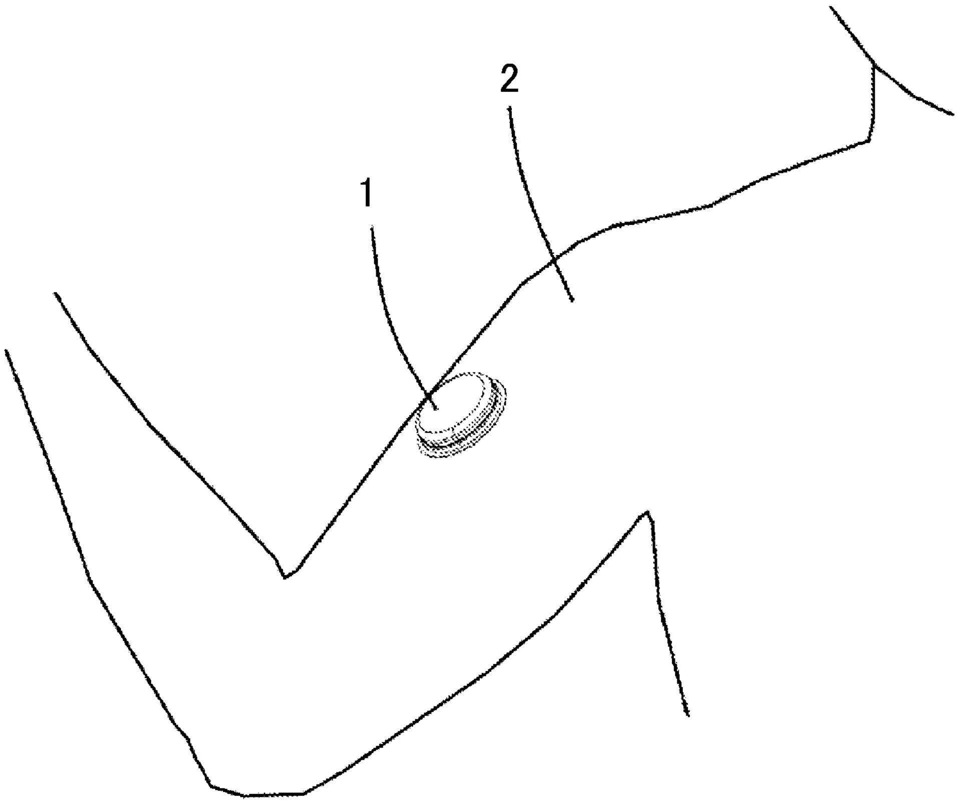
FIG. 1 illustrates an application example of a sensor according to Embodiment 1.

FIG. 1 illustrates an application example of sensor 1 according to Embodiment 1. In FIG. 1, living body 2 is illustrated as well as sensor 1. Living body 2 is, for example, a human body.

Sensor 1 illustrated in FIG. 1 is, for example, a biosensor. More specifically, sensor 1 is a CGM sensor. Sensor 1 is adapted such that a probe included in sensor 1 is inserted into living body 2 to continuously or semi-continuously measure glucose concentration in blood or an interstitial fluid of living body 2. For example, sensor 1 measures the glucose concentration of living body 2 for several days to several weeks.

Figure 2:
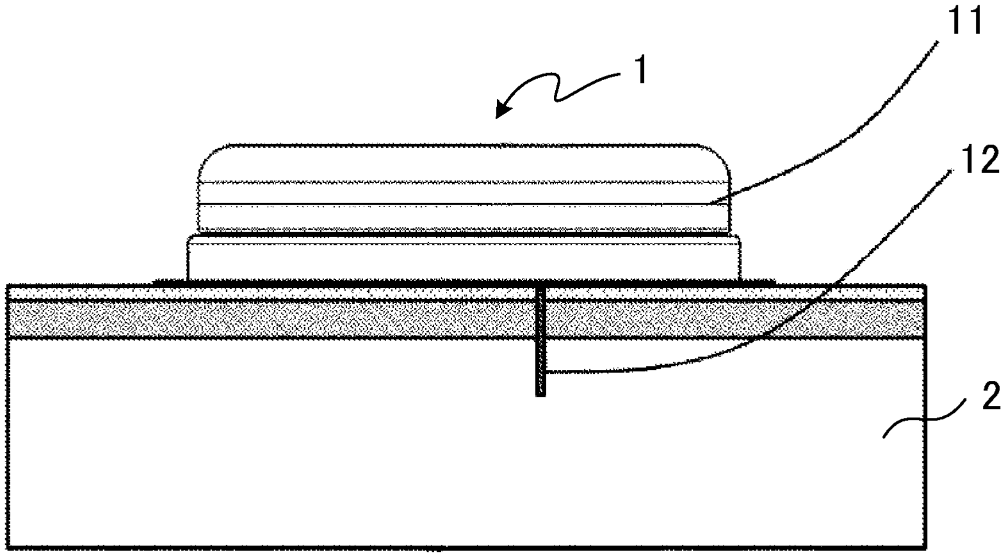
FIG. 2 illustrates a sectional view of the sensor.

FIG. 2 is a sectional view of sensor 1. In FIG. 2, the same reference signs are provided to the same components as those in FIG. 1.

As illustrated in FIG. 2, sensor 1 includes main body 11 and probe 12. Probe 12 is inserted into living body 2. Probe 12 includes a reagent layer containing oxidoreductase and outputs an electrical signal based on the glucose concentration to main body 11. Main body 11 stores, in a storage apparatus, the electrical signal based on the glucose concentration output from probe 12 and transmits the electrical signal to another apparatus (not illustrated) at a predetermined timing.

Figure 3:
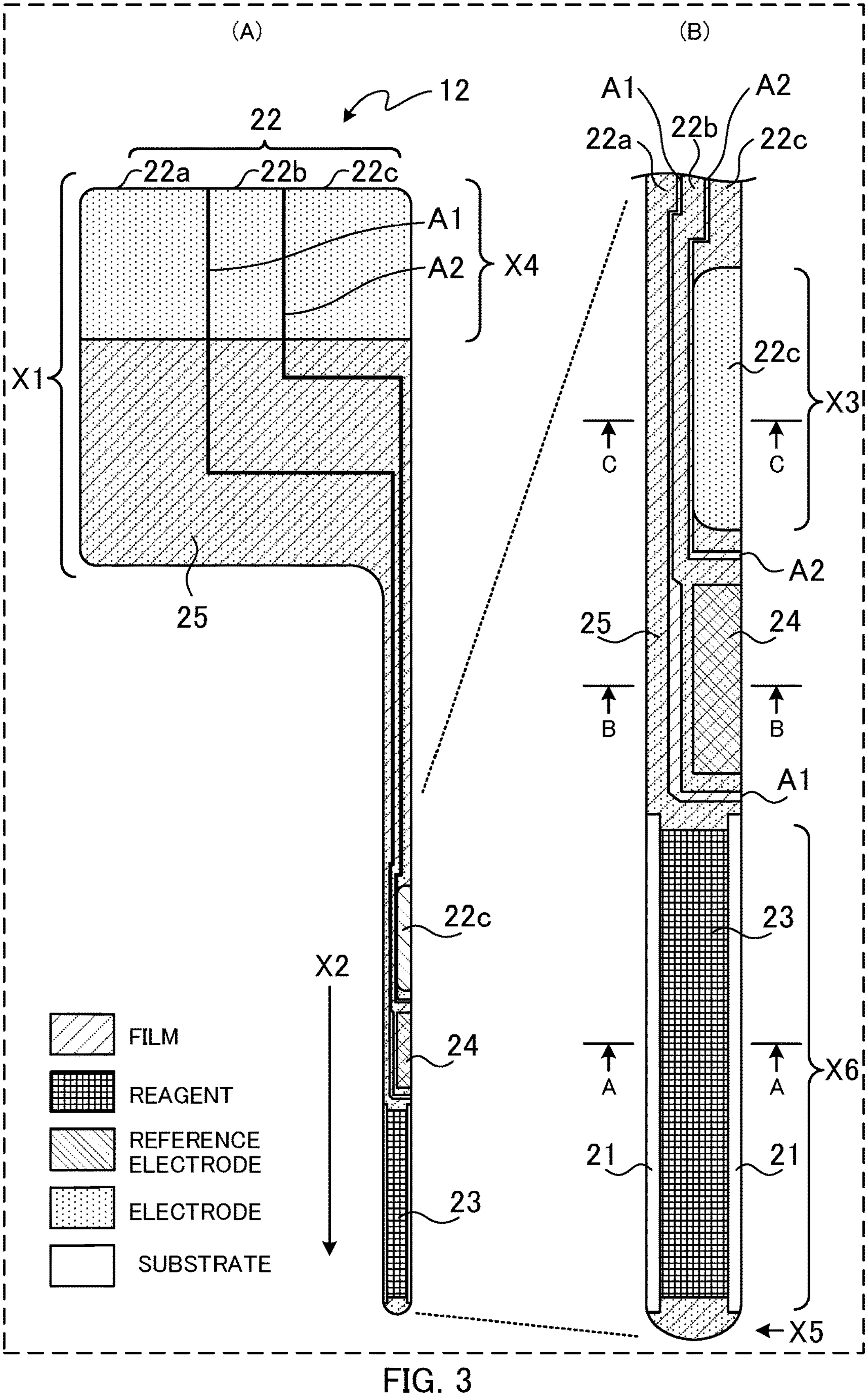
FIG. 3 illustrates plan views of a probe.

FIG. 3 illustrates plan views of probe 12. (A) of FIG. 3 illustrates entire probe 12. (B) of FIG. 3 illustrates an enlarged view of the distal end part of probe 12 illustrated in (A) of FIG. 3.

The part of region X1 (the head portion of probe 12) of probe 12 illustrated in (A) of FIG. 3 is accommodated in main body 11. The distal end part of probe 12 projects from main body 11. The distal end part of probe 12 is inserted into living body 2. Arrow X2 illustrated in (A) of FIG. 3 indicates an insertion direction of probe 12 into living body 2.

Probe 12 includes substrate 21, electrode 22, reagent layer 23, reference layer 24, and film 25.

A method for manufacturing probe 12 will be schematically described.

(1) Electrode 22 is Formed on Substrate 21.

Substrate 21 is, for example, a sheet-shaped synthetic resin. Electrode 22 is uniformly formed on substrate 21.

The material of electrode 22 is, for example, gold (Au). Electrode 22 may be formed on substrate 21 by sputtering, for example. Electrode 22 may be referred to as an electrode film or an electrode layer.

(2) Electrode 22 is Separated into Three Regions.

Grooves A1 and A2 are formed in electrode 22 formed on substrate 21 to separate electrode 22 into three regions. Electrode 22 is separated into working electrode 22*a*, reference electrode 22*b*, and counter electrode 22*c* by grooves A1 and A2. Grooves A1 and A2 may be formed by laser trimming, for example. Working electrode 22*a* may be referred to as a working electrode film or a working electrode layer. Reference electrode 22*b* may be referred to as a reference electrode film or a reference electrode layer. Counter electrode 22*c* may be referred to as a counter electrode film or a counter electrode layer.

Note that a potential (a potential with reference to the reference electrode) that is sufficient to oxidize a mediator (including not only an electronic mediator but also hydrogen peroxide) reduced by an analyte (glucose) reaction caused by oxidoreductase, for example, is provided to working electrode 22*a*. The glucose concentration is measured by monitoring a current flowing between working electrode 22*a* and counter electrode 22*c*.

(3) Reference Layer 24 is Formed.

Reference layer 24 is formed on reference electrode 22*b* at the distal end part of probe 12. The material of reference layer 24 is, for example, silver/silver chloride (Ag/AgCl). Reference layer 24 may be formed by a screen printing method or an ink jet method using an Ag/AgCl paste (ink), for example. Reference layer 24 may be referred to as a reference film or a reference electrode.

(4) Film 25 is Disposed and Fixed.

Film 25 having an opening is disposed on working electrode 22*a*, reference electrode 22*b*, counter electrode 22*c*, and reference layer 24 formed on substrate 21. Film 25 has a sheet shape and has an insulating property. Film 25 is disposed such that the opening part is located at the distal end part (the part forming reagent layer 23) of probe 12. A reagent, which will be described later, is dropped to the opening of film 25. Film 25 may be referred to as a film layer, an insulating layer, or an insulating film. The disposition may be referred to as lamination or placement instead.

Also, film 25 has an opening such that an upper surface (the surface in the front-side direction of the sheet surface in FIG. 3) of counter electrode 22*c* is partially exposed. The opening of film 25 is cut into a notch shape as illustrated in region X3 in (B) of FIG. 3 in the cutting process (7), which will be described later. With the notch shape, a part of counter electrode 22*c* is exposed in the upper surface. Note that the upper surface may be considered as a surface of probe 12 on a side on which reagent layer 23 is formed.

Also, film 25 has such a shape that the head portion of probe 12 is partially exposed. For example, the part of region X4 in (A) of FIG. 3 is not covered with film 25. Exposed electrode 22 in region X4 is connected to a circuit of main body 11.

Note that the upper surface of reference layer 24 is covered with film 25 as illustrated in (B) of FIG. 3. Reference layer 24 is exposed in the width direction of probe 12 (the direction that is orthogonal to the insertion direction illustrated by arrow X2). In the example in (B) of FIG. 3, reference layer 24 is exposed to the right side surface of the distal end part of probe 12 (see reference layer 24 in FIG. 4B as well).

(5) Reagent Layer 23 is Formed.

Reagent layer 23 is formed on working electrode 22*a* at the distal end part of probe 12. For example, a reagent is dropped to the opening of film 25, which will be described above, and is then dried to thereby form reagent layer 23. It is preferable that reagent layer 23 be not formed at the distal end of probe 12 illustrated by arrow X5 in (B) of FIG. 3. In other words, reagent layer 23 is preferably formed to be separated from the distal end of probe 12. In other words, it is preferable that reagent layer 23 be not formed in a predetermined distance from the distal end of probe 12. This is because it is possible to curb peeling-off (turning-up) of reagent layer 23 from probe 12 when probe 12 is inserted into living body 2 by forming reagent layer 23 to be separated from the distal end of probe 12.

Reagent layer 23 contains at least oxidoreductase capable of causing an oxidation-reduction reaction with the analyte (glucose). Reagent layer 23 may be referred to as a reagent film, a working layer, or a working electrode.

Note that the opening of film 25 may have such a size and a shape that reagent layer 23 with a larger width than the width of probe 12, for example, is formed. Reagent layer 23 formed to have a larger width than that of probe 12 is shaped in the next trimming process.

(6) Reagent Layer 23 and Electrode 22 are Removed.

Reagent layer 23 and electrode 22 are trimmed along the insertion direction of probe 12 at an end in the width direction of probe 12 with the outer shape formed in the cutting process (7), which will be described later. The upper surface of substrate 21 is partially exposed as illustrated in region X6 in (B) of FIG. 3 through the trimming. For the trimming of reagent layer 23 and electrode 22, laser trimming, for example, may be used.

Note that in (B) of FIG. 3, film 25 is also partially (a little) trimmed at both end parts of reagent layer 23 in the insertion direction.

(7) Probe 12 is Cut Out of Substrate 21 Through Cutting.

Substrate 21 after the above processes (1) to (6) is cut into probe 12 with the shape illustrated in (A) of FIG. 3.

The cutting position includes the trimmed part. For example, a part near the center (near the center line) of the trimmed part (the bottom part of the recess) is cut.

(8) A Protective Film is Formed.

A liquid for forming the protective film, for example, is applied to the distal end part of cut probe 12 to form the protective film. The protective film prevents or curbs leakage of substances (mainly, oxidoreductase and the electron mediator) contained in reagent layer 23 to the outside of the protective film. The protective film has a hole that transmits the analyte that is present outside the protective film into the protective film where reagent layer 23 is present. It is only necessary for the protective film to be able to protect (cover) at least the part corresponding to reagent layer 23 in probe 12.

Figure 4A:
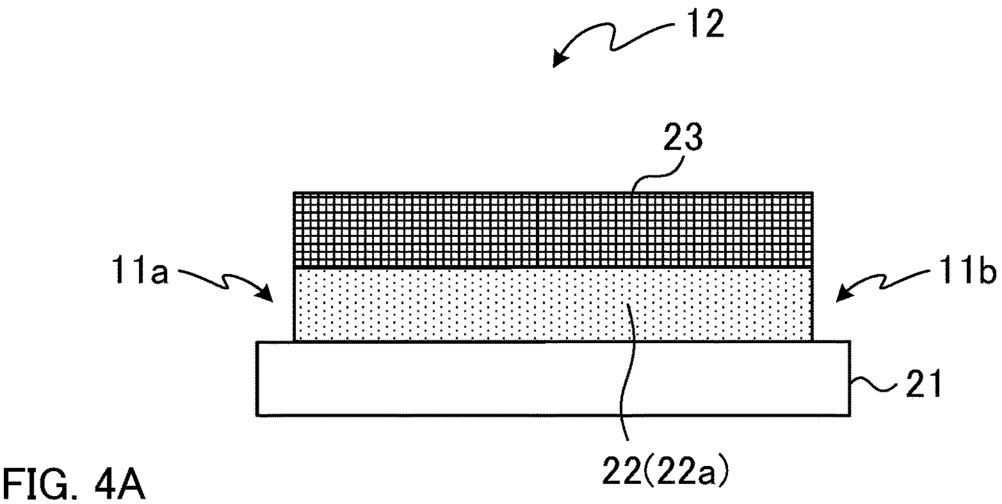
FIG. 4A illustrates a sectional view along arrow AA in FIG. 3.

FIG. 4A is a sectional view along arrow AA in FIG. 3. As illustrated in FIG. 4A, working electrode 22*a* is formed on (the upper surface of) substrate 21 at the part of probe 12 where reagent layer 23 is formed. Reagent layer 23 is formed on working electrode 22*a*.

Reagent layer 23 and working electrode 22*a* are removed at both ends of probe 12 in the width direction (side surfaces of probe 12) in the trimming process (6) described above. In the cutting process (7) described above, substrate 21 exposed in the trimming process (6) described above is cut at a position separated from reagent layer 23 and working electrode 22*a*. In this manner, the side surfaces of probe 12 has stepped shapes as illustrated by arrows 11*a* and 11*b* in FIG. 4A.

Note that the protective film is formed in the surroundings of the distal end part of probe 12 at reagent layer 23. In FIG. 4A, illustration of the protective film is omitted.

Figure 4B:
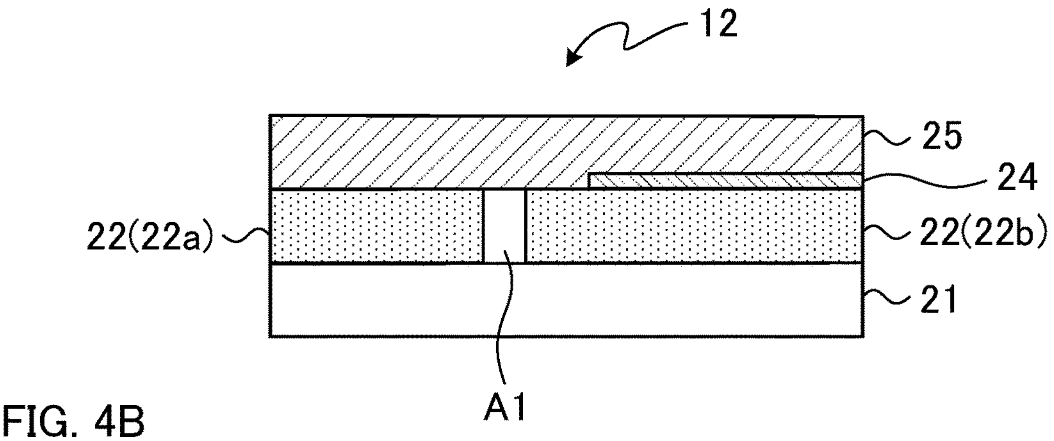
FIG. 4B illustrates a sectional view along arrow BB in FIG. 3.

FIG. 4B is a sectional view along arrow BB in FIG. 3. As illustrated in FIG. 4B, working electrode 22*a* and reference electrode 22*b* are formed on substrate 21 at the part of probe 12 where reference layer 24 is formed. Working electrode 22*a* and reference electrode 22*b* are physically and electrically separated by groove A1.

Reference layer 24 is disposed on reference electrode 22*b*. Film 25 is formed on working electrode 22*a*, reference electrode 22*b*, and reference layer 24. Reference layer 24 includes the upper surface covered with film 25 and includes a side surface (the right side surface in FIG. 4B) of probe 12 exposed.

Note that film 25 at the upper portion of reference layer 24 may not be provided. In other words, the upper surface of reference layer 24 may be exposed.

Figure 4C:
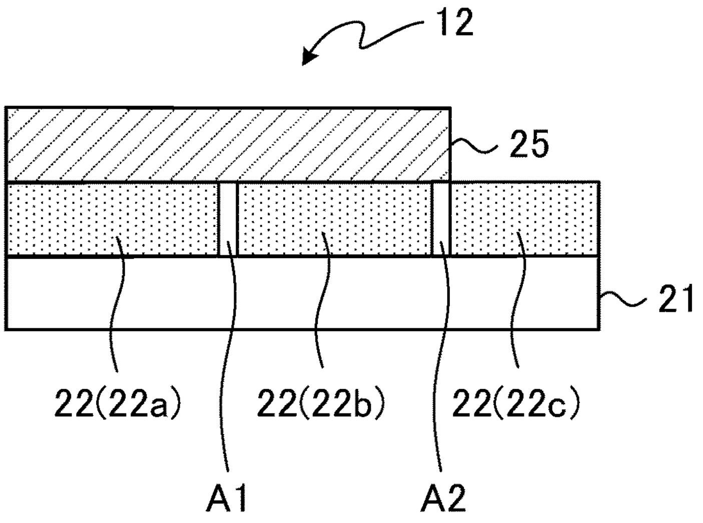
FIG. 4C illustrates a sectional view along arrow CC in FIG. 3.

FIG. 4C is a sectional view along arrow CC in FIG. 3. As illustrated in FIG. 4C, working electrode 22*a*, reference electrode 22*b*, and counter electrode 22*c* are formed on substrate 21 at the part where the upper surface of counter electrode 22*c* is exposed. Working electrode 22*a* and reference electrode 22*b* are physically and electrically separated by groove A1. Reference electrode 22*b* and counter electrode 22*c* are physically and electrically separated by groove A2.

Film 25 is formed on working electrode 22*a* and reference electrode 22*b*. Film 25 is not disposed on counter electrode 22*c*, and the upper surface of counter electrode 22*c* is exposed.

Examples of each component will be described.

Substrate 21

Substrate 21 is a synthetic resin on a sheet. For example, polyethylene terephthalate (PET) may be used for substrate 21. However, the resin material is not particularly limited as long as the resin material has at least one or more features of flexibility, easiness of working, and heat resistance like a plastic material. Other examples include general-purpose plastic such as polyethylene, polypropylene, and polyethylene naphthalate. In a case in which high heat resistance is needed, polyimide is preferably used.

Electrode 22

As a material of electrode 22, gold may be used as described above. However, the material is not particularly limited as long as the material is a metal or carbon material with electrical conductivity and stability (for example, it is unlikely to be oxidized or has salinity tolerance). Examples of the material of electrode 22 include platinum, palladium, and carbon.

In a case in which a metal material is used for electrode 22, the metal material may be deposited (including sputtering) on substrate 21. Other formation methods include printing, plating, and spin coating.

In a case in which carbon is used for electrode 22, electrode 22 may be formed by printing a carbon paste. In a case in which one of the upper surface and the back surface of probe 12 is caused to serve as a working electrode and the other surface is caused to serve as a counter electrode, different electrode materials may be used for the working electrode and the counter electrode.

Reagent Layer 23

Reagent layer 23 contains oxidoreductase capable of causing an oxidation-reduction reaction with at least the analyte as described above. If oxidoreductase is dehydrogenase, an electronic mediator is further contained. Reagent layer 23 may be a system using an electronic mediator even if oxidoreductase is oxidase. In other words, although the electronic mediator is not needed by a system that electrochemically detects hydrogen peroxide generated by the oxidation-reduction reaction of glucose caused by oxidase, electrochemical detection may also be performed using the electronic mediator. In this case, reagent layer 23 includes the electronic mediator in addition to oxidase.

For the system detecting glucose, examples of oxidoreductase include glucose oxidase and glucose dehydrogenase. In regard to glucose dehydrogenase, it is desirable to use flavin adenine dinucleotide (FAD)-bound glucose dehydrogenase, and for example, enzymes derived from the genus *Aspergillus* (*oryzae* or *terreus*) or the genus *Mucor* are preferably used, in terms of low reactivity with respect to maltose.

Examples of the electronic mediator include osmium complexes, ruthenium complexes, quinone compounds, phenazine compounds, and ferrocene compounds. Also, examples of the electronic mediator include derivatives and the like thereof Reference Layer 24

As a material of reference layer 24, silver/silver chloride (Ag/AgCl) may be used as described above. Reference layer 24 may be formed by screen-printing or applying an Ag/AgCl paste (ink) on or to electrode 22 and then drying it. As another formation method, reference layer 24 may be formed by performing printing, applying, plating, or the like of silver (Ag) on electrode 22 and then performing chlorination on the surface thereof.

Note that although the example in which sensor 1 according to the present disclosure has the three-electrode configuration, namely the working electrode, the counter electrode, and the reference electrode for realizing highly accurate measurement has been described, sensor 1 may have a two-electrode configuration, namely the working electrode and the counter electrode.

Film 25

As film 25, a product obtained by attaching an adhesive sheet (an acrylic-based, rubber-based, or hot melt-based adhesive sheet, for example) to a sheet of the same material as that of substrate 21 may be used. Also, a sheet of a material that is different from that of substrate 21 may be used. The adhesive sheet may be used alone as film 25. A thermoplastic/photoplastic resist film may be used as film 25.

Film 25 preferably has a contact angle with a liquid on the film that is greater than a contact angle with a liquid at the opening, and a greater difference therebetween is more preferable, in terms of application of the reagent, for example. For example, it is desirable that the contact angle with the liquid on the film be equal to or greater than 90° and the contact angle with the liquid at the opening be equal to or less than 50°. Even if the material does not have such a contact angle, it is also possible to cause the material to have the contact angle by performing at least one of a water repellent treatment on the film surface and a hydrophilic treatment on the opening.

Film 25 has a thickness of equal to or greater than 1 μm and equal to or less than 150 μm, preferably has a thickness of equal to or greater than 3 μm and equal to or less than 50 μm, and more preferably has a thickness of equal to or greater than 5 μm and equal to or less than 30 μm. Film 25 may be formed by printing a resist ink.

Protective Film

Probe 12 having reagent layer 23 is used by being inserted into living body 2. Therefore, the protective film covering the surface of reagent layer 23 preferably has living body adaptability with which protein and cells are not adsorbed thereto or are unlikely to be adsorbed thereto. In general, the protective film is preferably formed of a polymer having characteristics as described above.

Examples of the polymer include a copolymer of methyl methacrylate and hydroxyethyl methacrylate, a copolymer of butyl methacrylate and hydroxyethyl methacrylate, and poly(2-methacryloyloxyethyl phosphorylcholine-co-n-butyl methacrylate). Note that it is also possible to use a (meth) acrylate-based compound having a similar principal chain to that of these exemplified polymers and having, as a side chain, a reactive group capable of causing a reaction with a linker as an "ethylene-based polymer" having a methacryloyl group or an acryloyl group, which is exemplified as a specific example of a high-molecular-weight polymer.

Figure 5:
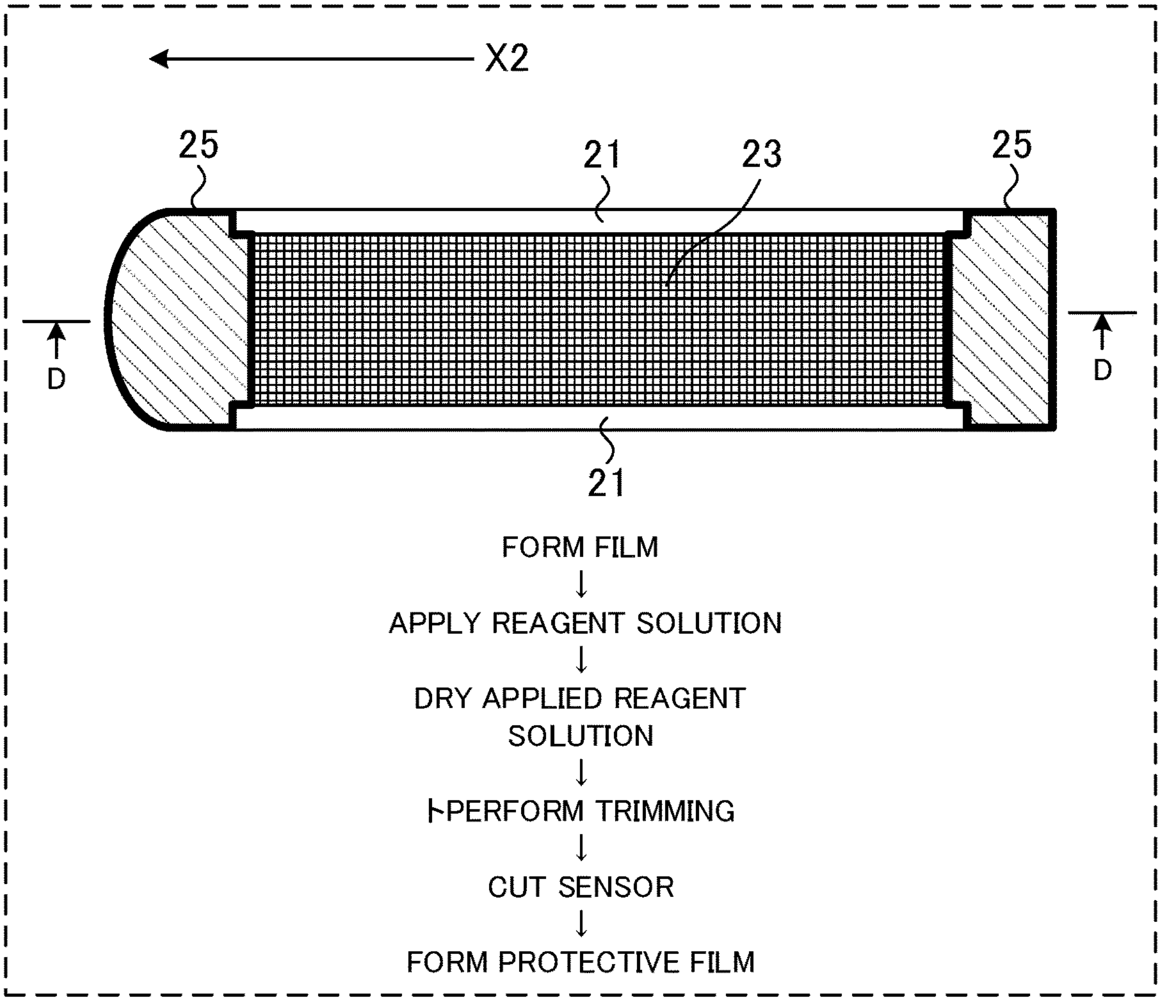
FIG. 5 describes a positional relationship between a reagent layer and a film.

FIG. 5 describes a positional relationship between reagent layer 23 and film 25. FIG. 5 illustrates a plan view of the distal end part of probe 12. In FIG. 5, the same reference signs are provided to the same components as those in FIG. 3.

FIG. 5 illustrates a part of a process of manufacturing probe 12. "Formation of film" illustrated in FIG. 5 corresponds to the aforementioned process (4). "Apply reagent solution" and "dry applied reagent solution" correspond to the aforementioned process (5). "Perform trimming" corresponds to the aforementioned process (6). "Cut sensor" corresponds to the aforementioned process (7). "Form protective film" corresponds to the aforementioned process (8).

Note that in FIG. 5, description of the aforementioned processes (1) to (3) is omitted. The process "form film" follows the aforementioned processes (1) to (3). Also, illustration of the protective film is omitted in FIG. 5.

Figure 6:
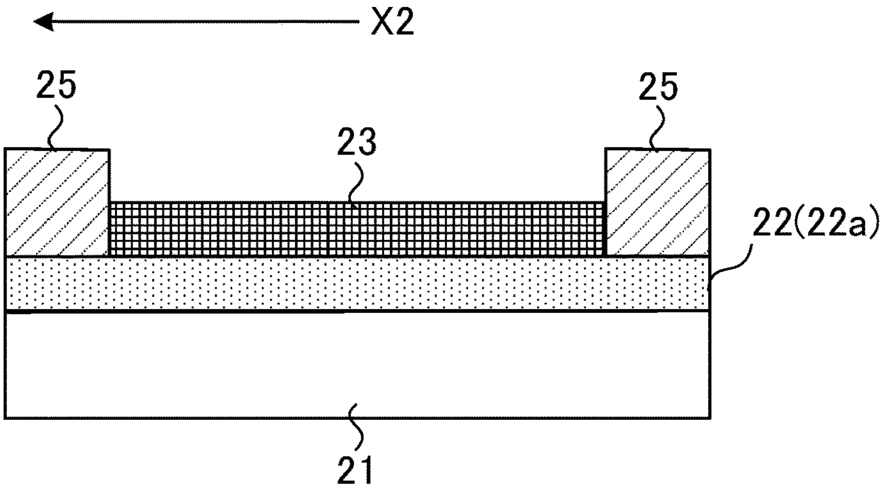
FIG. 6 illustrates a sectional view along arrow DD in FIG. 5.

FIG. 6 is a sectional view along the arrow DD in FIG. 5. Film 25 having the opening is disposed on working electrode 22*a*. The reagent is dropped onto the opening part of film 25 and is then dried. In this manner, reagent layer 23 is formed with reagent layer 23 interposed in film 25 in the insertion direction of probe 12 as illustrated in FIG. 6. In other words, reagent layer 23 is formed with reagent layer 23 accommodated in a region defined by the opening of film 25. In other words, film 25 is adjacent to reagent layer 23 on electrode 22.

Note that film 25 on the side of the insertion direction may not be formed. For example, film 25 on the left side illustrated in FIGS. 5 and 6 may be omitted.

Figure 7:
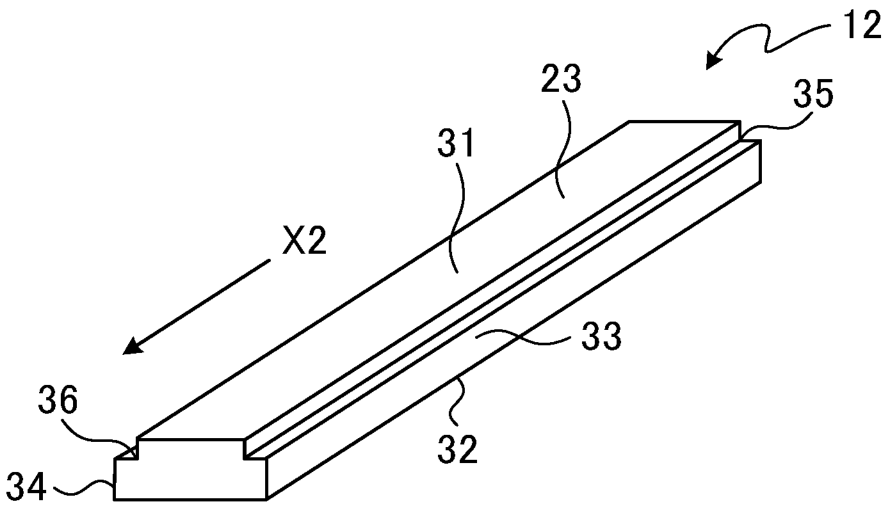
FIG. 7 illustrates a perspective view of a reagent layer part of the probe.

FIG. 7 illustrates a perspective view of the part corresponding to reagent layer 23 of probe 12. As illustrated in FIG. 7, probe 12 includes upper surface 31 on which reagent layer 23 is formed, back surface 32 that faces upper surface 31, side surface 33 that connects upper surface 31 to back surface 32, and side surface 34 that faces side surface 33 and connects upper surface 31 to back surface 32. Arrow X2 illustrated in FIG. 7 indicates the insertion direction of probe 12 into living body 2.

End portions of upper surface 31 of probe 12 in the width direction have stepped trimmed portions 35 and 36 from which reagent layer 23 and electrode 22 have been removed. Trimmed portions 35 and 36 are formed with a positional relationship with which they are in contact at least with reagent layer 23. In other words, reagent layer 23 extends from an end to the other end in the width direction of upper surface 31 to form upper surface 31 of probe 12 and also forms a part of the side surfaces of probe 12 (see reagent layer 23 in FIG. 4A as well).

Sensor 1 described above may be regarded as including the following components.

Sensor 1 includes main body 11 and probe 12. Probe 12 is inserted into living body 2 and acquires an electrical signal for continuously or semi-continuously measuring an analyte.

Substrate 21 includes a first surface (for example, upper surface 31) and a second surface (for example, back surface 32) facing the first surface. Also, substrate 21 includes a third surface and a fourth surface (for example, side surfaces 33 and 34) that are surfaces connecting the first surface to the second surface and extending in the insertion direction of probe 12.

Working electrode 22*a* is formed of a first electrode material on the first surface of substrate 21.

Reagent layer 23 is disposed at a part of working electrode 22*a*.

Trimmed portions 35 and 36 are formed at both end portions of the first surface in a direction that is orthogonal to the direction along the insertion direction of probe 12 into living body 2 by reagent layer 23 and the first electrode material being removed.

Reagent layer 23 contains oxidoreductase. Trimmed portions 35 and 36 are formed with a positional relationship with which they are in contact at least with reagent layer 23.

Film 25 is adjacent to reagent layer 23 in a direction opposite to the distal end side of probe 12 in the insertion direction into living body 2.

Reagent layer 23 does not have a part interposed between electrode 22 and film 25. In other words, film 25 is not disposed on reagent layer 23. Film 25 may or may not be adjacent to reagent layer 23 on the distal end side of probe 12. In other words, film 25 may or may not be formed on the distal end side of probe 12.

Sensor 1 described above may be regarded as including the following manufacturing process.

First, substrate 21 (substrate sheet) with working electrode 22*a* of the first electrode material formed on the first surface is prepared.

Next, a reagent solution containing oxidoreductase is applied to a predetermined position on the first surface.

Then, the reagent solution is dried to thereby form reagent layer 23.

Next, the predetermined positions of reagent layer 23 on substrate 21 are trimmed to form trimmed portions, from which reagent layer 23 and working electrode 22*a* formed below reagent layer 23 have been removed.

Next, substrate 21 is cut into a predetermined shape (the shape of probe 12 illustrated in (A) of FIG. 3, for example, a flagpole shape). The position at which substrate 21 is cut includes trimmed portions 35 and 36.

Note that a protective film may be formed at the distal end part of probe 12 where reagent layer 23 is formed. The protective film includes a hole that can transmit at least an analyte (glucose) therethrough.

Also, counter electrode 22*c* may be formed on the first surface of substrate 21 or may be formed on the second surface. Another counter electrode (second counter electrode) that is different from the counter electrode 22*c* may be formed on both or one of the first surface and the second surface of substrate 21.

Also, reference electrode 22*b* may be formed on at least one of the first to fourth surfaces. In a case in which reference layer 24 is formed on the first surface, film 25 may be disposed on the upper surface with the third surface side exposed.

Also, reagent layer 23 may not be formed in a predetermined distance from the terminal end side (the distal end of probe 12) of the first surface in the insertion direction of probe 12.

A part (end portion) of reagent layer 23 may be interposed between electrode 22 and film 25. Reagent layer 23 may not have a part interposed between electrode 22 and film 25.

As described above, sensor 1 includes probe 12 that is to be inserted into living body 2 to measure an analyte. Probe 12 includes substrate 21, electrode 22 that is formed on substrate 21, and reagent layer 23 that contains oxidoreductase and is formed on electrode 22. Reagent layer 23 and electrode 22 of probe 12 are trimmed at least one of end portions in the width direction along the insertion direction of probe 12 into living body 2.

In this manner, variations of performance of sensor 1 caused by the manufacturing process are reduced. For example, even if a so-called coffee ring state in which reagent layer 23 dropped onto electrode 22 is thicker at its edge part than at its center portion is achieved, it is possible to use a uniform (even) part inside the ring as reagent layer 23 by the trimming.

Also, it is possible to prevent a blade tip from coming into contact with reagent layer 23 at the time of the cutting into the shape of probe 12 and to reduce cracking of reagent layer 23.

Also, it is possible to prevent the blade tip from coming into contact with reagent layer 23 at the time of the cutting into the shape of probe 12 and to reduce contamination of the reagent.

As described above, probe 12 included in sensor 1 is manufactured by a process of forming electrode 22 on substrate 21, a process of forming reagent layer 23 containing oxidoreductase on electrode 22, and a process of trimming reagent layer 23 and electrode 22 from at least one of end portions of probe 12 in the width direction along the insertion direction of probe 12 into living body 2.

In this manner, variations in performance of sensor 1 caused by the manufacturing process are reduced. For example, even if reagent layer 23 dropped onto electrode 22 is brought into the coffee ring state, it is possible to use a uniform (even) center part inside the ring as reagent layer 23 by the trimming.

It is possible to prevent the blade tip from coming into contact with reagent layer 23 by the trimming at the time of the cutting into the shape of probe 12 and thereby to reduce cracking of reagent layer 23. Also, it is possible to reduce contamination of the reagent.

As described above, film 25 is disposed on electrode 22 such that it is adjacent to reagent layer 23 at both end portions of reagent layer 23 in the insertion direction.

In this manner, variations in performance of sensor 1 caused by the manufacturing process are reduced. For example, it is possible to determine, by film 25, the position at which the reagent is to be dropped and to form uniform reagent layer 23 before the trimming.

Modification Example 1

Probe 12 may have a trimmed portion at one of the ends in the width direction. In other words, there may be one trimmed portion.

Figure 8:
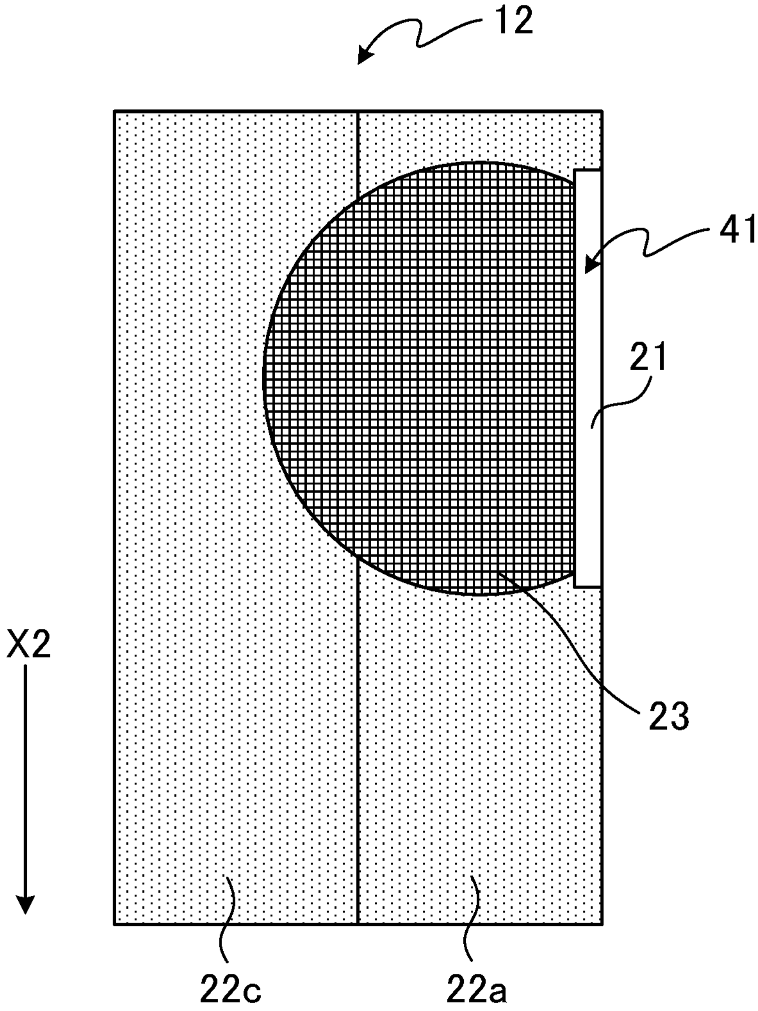
FIG. 8 illustrates a plan view of a distal end part of the probe.

FIG. 8 illustrates a plan view of the distal end part of probe 12. In FIG. 8, the same reference signs are provided to the same components as those in FIG. 3. FIG. 8 illustrates an example in which working electrode 22*a* and counter electrode 22*c* are formed in an aligned manner in the width direction of probe 12. In FIG. 8, illustration of film 25 is omitted.

Reagent layer 23 is formed to cross over the width of probe 12 on one end side of probe 12 in the width direction. Reagent layer 23 is formed not to cross over the width of probe 12 on the other end side of probe 12 in the width direction. In the example of FIG. 8, reagent layer 23 is formed to cross over the right end of probe 12 and is formed not to cross over the left end of probe 12, for example.

Probe 12 includes trimmed portion 41. Trimmed portion 41 is formed on the side on which reagent layer 23 crosses over the width of the probe (the right side in FIG. 6). Trimmed portion 41 is formed by trimming reagent layer 23 and working electrode 22*a*. Substrate 21 is exposed by trimmed portion 41.

In this manner, probe 12 may have the trimmed portion at one of the ends in the width direction. This also leads to reduction of variations in performance of sensor 1 caused by the manufacturing process.

Modification Example 2

Reagent layer 23 may stick out of the region defined by film 25 in the insertion direction of probe 12.

Figure 9:
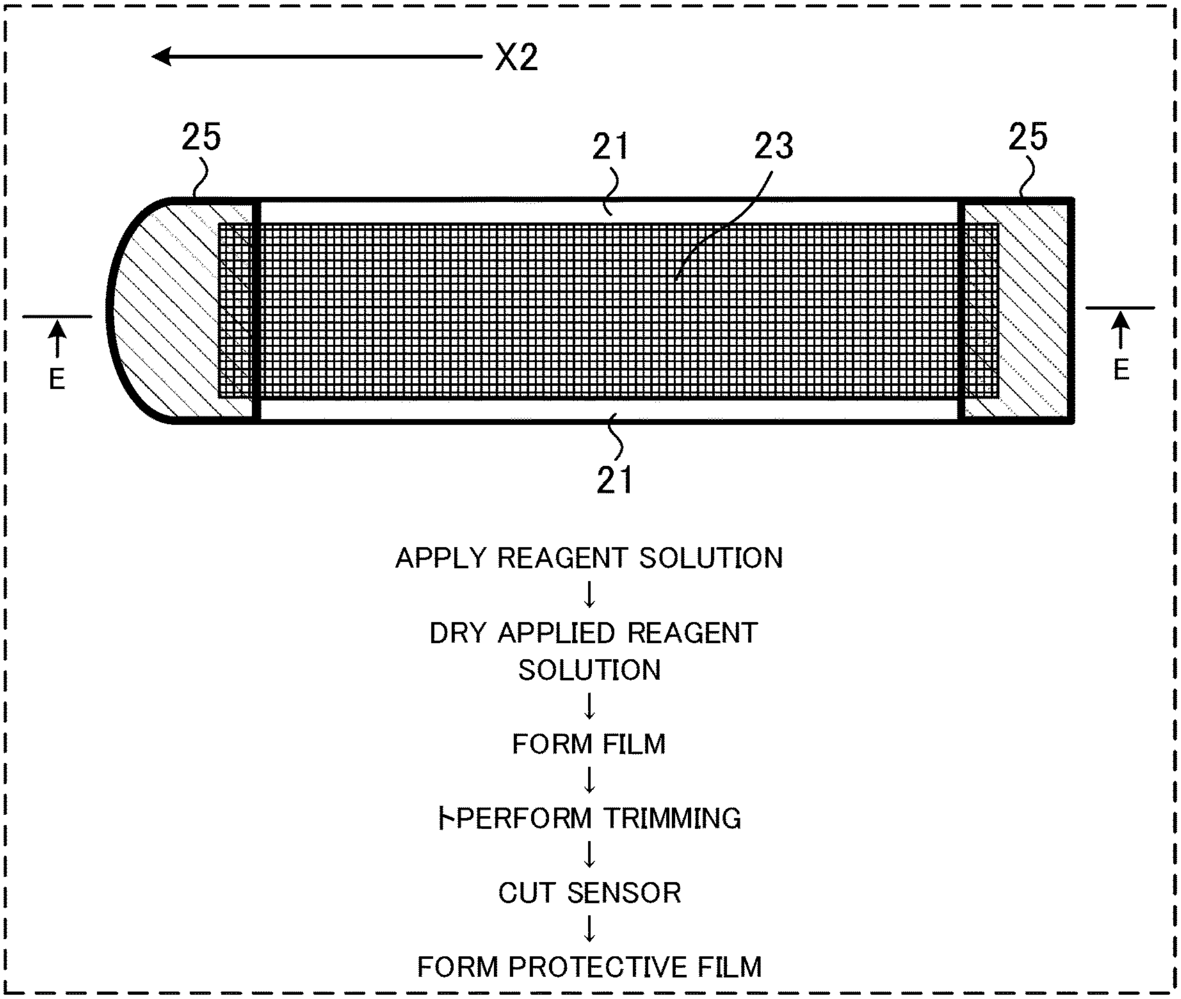
FIG. 9 describes the positional relationship between the reagent layer and the film.

FIG. 9 is a diagram for describing a positional relationship between reagent layer 23 and film 25. FIG. 9 illustrates a plan view of the distal end part of probe 12. In FIG. 9, the same reference signs are provided to the same components as those in FIG. 3.

FIG. 9 illustrates a part of the process of manufacturing probe 12. "Apply reagent fluid" and "dry applied reagent" illustrated in FIG. 9 correspond to the aforementioned process (5). "Form film" corresponds to the aforementioned process (4). "Perform trimming" corresponds to the aforementioned process (6). "Cut sensor" corresponds to the aforementioned process (7). "Form protective film" corresponds to the aforementioned process (8).

Note that in FIG. 9, description of the aforementioned processes (1) to (3) is omitted. The process "apply reagent solution" illustrated in FIG. 9 follows the aforementioned processes (1) to (3). Also, illustration of the protective film is omitted in FIG. 9.

Figure 10:
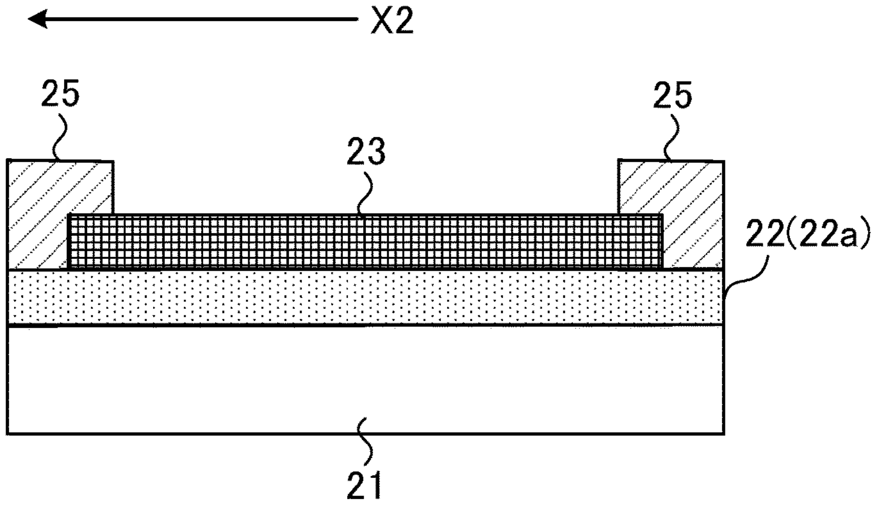
FIG. 10 illustrates a sectional view along arrow EE in FIG. 9.

FIG. 10 illustrates a sectional view along arrow EE in FIG. 9. Film 25 having an opening is disposed on reagent layer 23. Film 25 is disposed such that the opening part is located at reagent layer 23. The opening of film 25 is formed to overlap reagent layer 23 at both ends of reagent layer 23 in the insertion direction (the direction of arrow X2). In other words, a part of film 25 overlaps reagent layer 23 at both ends of reagent layer 23 in the insertion direction. Also, a part of film 25 overlaps the trimmed portions at both ends of the trimmed portions in the insertion direction.

Note that film 25 on the side of the insertion direction may not be formed. For example, film 25 on the left side illustrated in FIGS. 9 and 10 may be omitted.

In this manner, film 25 is disposed on electrode 22 to overlap reagent layer 23 and trimmed portions at both end portions of reagent layer 23 in the insertion direction.

In this manner, variations in performance of sensor 1 caused by the manufacturing process are reduced. For example, it is possible to cover the end portions (the edge parts of the coffee ring) of reagent layer 23 in the insertion direction of probe 12 with film 25 and expose the uniform part of reagent layer 23.

Modification Example 3

Examples of the opening shape of film 25 will be described.

Figure 11:
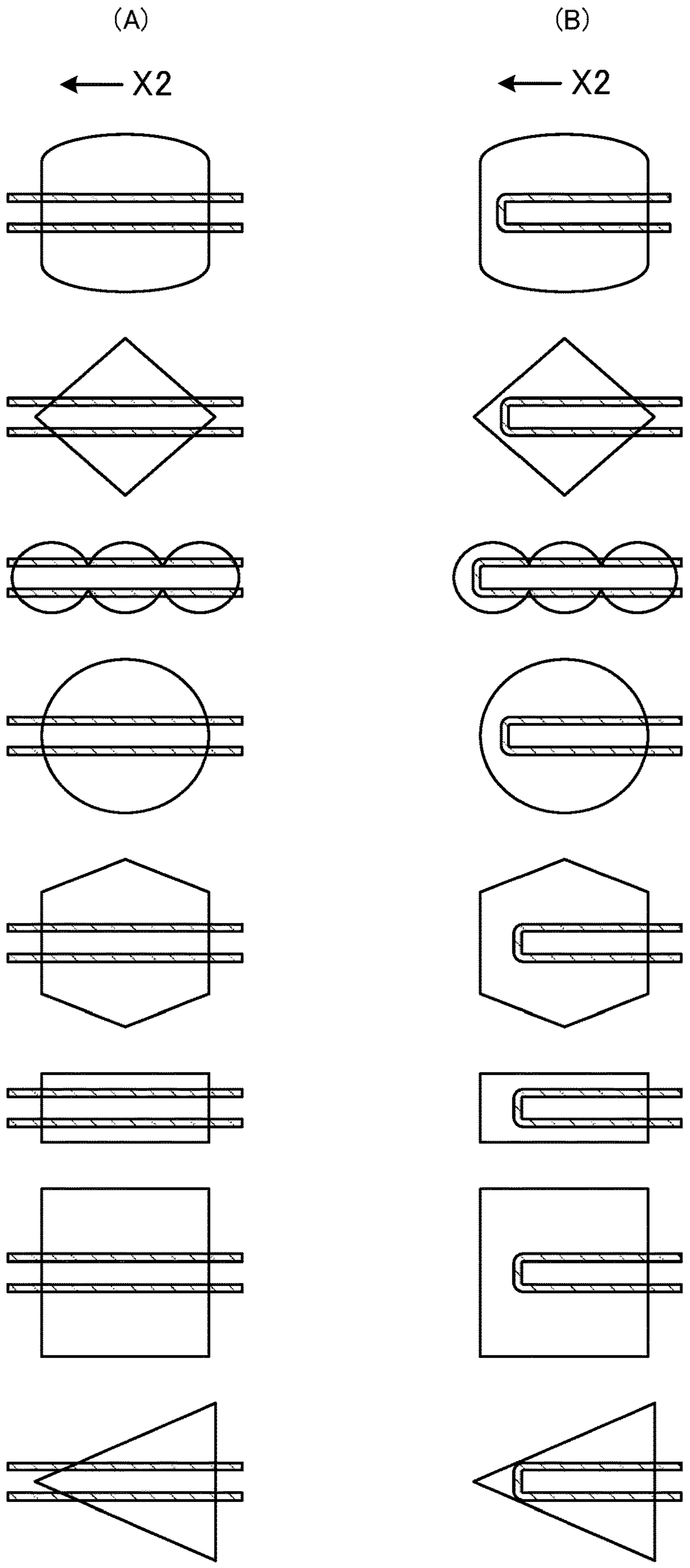
FIG. 11 illustrates examples of an opening shape of the film.

FIG. 11 illustrates examples of the opening shape of film 25. The hatched parts in (A) of FIG. 11 and (B) of FIG. 11 illustrate trimmed portions. The figures with polygonal shapes, circular shapes, and the like illustrated in (A) of FIG. 11 and (B) of FIG. 11 illustrate the shapes of the opening part of film 25. Arrow X2 illustrated in FIG. 11 indicates the insertion direction of probe 12 into living body 2.

In (A) of FIG. 11, film 25 is formed at both ends of reagent layer 23 in the insertion direction (see FIGS. 5 and 6, for example). In (B) of FIG. 11, film 25 is formed at an end on a side opposite to the distal end side of reagent layer 23 (film 25 is formed on the right side in FIGS. 5 and 6 and film 25 on the left side is not formed, for example). In this manner, the opening shape of film 25 may be various shapes.

Modification Example 4

An example of the size of sensor 1 will be described.

Figure 12:
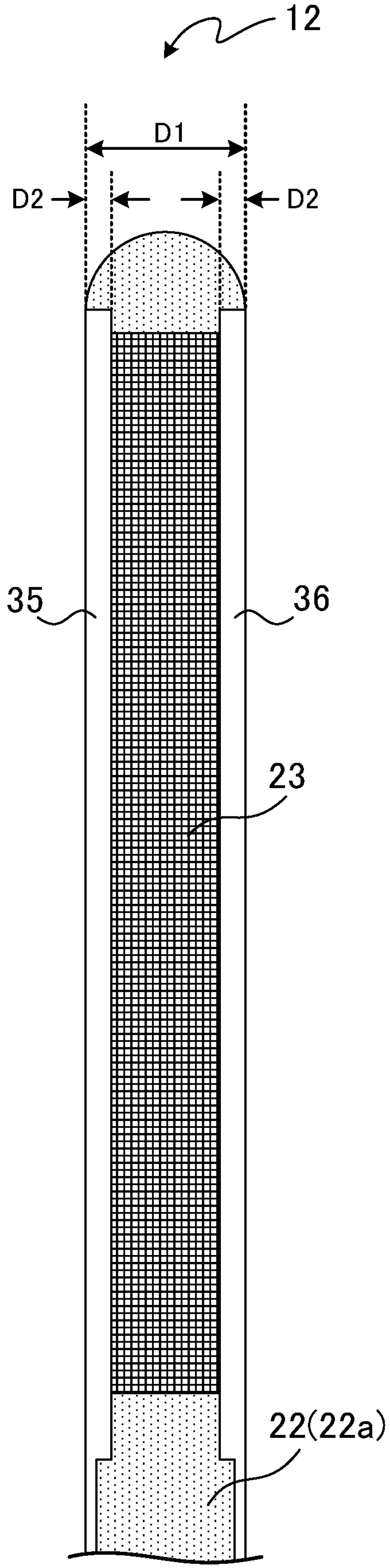
FIG. 12 describes an example of a sensor size.

FIG. 12 describes an example of the size of sensor 1. In FIG. 12, the same reference signs are provided to the same components as those in FIGS. 3 and 7. In FIG. 12, illustration of film 25 is omitted.

Width D1 of distal end part of probe 12 is, for example, equal to or greater than 70 μm and equal to or less than 1700 μm. Width D1 is preferably equal to or greater than 70 μm and equal to or less than 600 μm and is more preferably equal to or greater than 70 μm and equal to or less than 400 μm.

Width D2 of trimmed portions 35 and 36 is, for example, equal to or greater than 5 μm. Width D2 is not particularly limited as long as a condition of a width with which it is possible to secure reagent layer 23 with respect to the width of the distal end part of probe 12 is met. In a case in which it is desired to widen width D2 of trimmed portions 35 and 36, it can be realized by performing irradiation with a laser a plurality of times.

Embodiment 2

In Embodiment 2, a protective film covering the outer circumference of a probe will be described. The protective film may be referred to as a living body protective film.

The protective film has a hole with a size with which a low-molecular compound can be transmitted therethrough. For example, the protective film has a hole with a size with which glucose that is an analyte can be transmitted therethrough. In this manner, glucose outside the probe can be transmitted through the protective film and reach the probe.

On the other hand, the hole of the protective film has a size with which oxidoreductase or the like contained in the reagent layer cannot be transmitted therethrough or oxidoreductase or the like is unlikely to be transmitted therethrough. Therefore, the sensor (probe) such as a CGM sensor embedded in the living body measures the concentration and the like of glucose with the protective film and prevents the reagent in the reagent layer formed at the probe from leaking to the living body.

It is only necessary for the protective film to be formed on (cover) at least the part covering the reagent layer in the sensor such as a CGM sensor. Therefore, the formation of the protective film may be performed by a dipping technique.

For example, a protective film component is dissolved in an organic solvent such as ethanol, and the probe is immersed into the protective film solution. The immersing into the protective film solution and drying are repeated a plurality of times to thereby form the protective film with a desired thickness on the probe surface.

However, the manufacturing process for the formation of the protective film based on the dipping technique is complicated. Also, the thickness and the shape of the protective film of each sensor may vary, which may lead to variations in performance.

For example, although it is possible to reduce variations in the protective film by using a protective film solution with low concentration of the protective film component and increasing the number of times the immersing and the drying are repeated, the increase in number of times of the immersing and the drying leads to a complicated manufacturing process. On the other hand, if a protective film solution with high concentration of the protective film component is used, and the number of times the immersing and the drying are repeated is reduced in order to simplify the manufacturing process, the thickness and the shape of the protective film may vary, which leads to variations in performance.

Hereinafter, a sensor, for which it is possible to simply manufacture a protective film, which reduces variations in performance and a method for manufacturing the same will be described.

Figure 13:
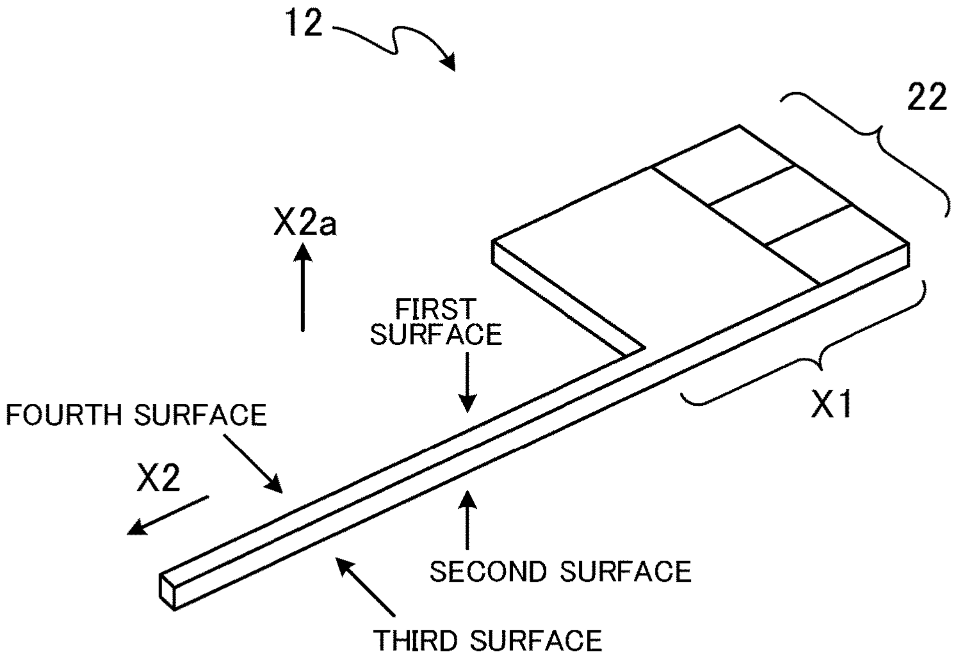
FIG. 13 illustrates a perspective view of a probe of a sensor according to Embodiment 2.

FIG. 13 illustrates a perspective view of probe 12 of sensor 1 according to Embodiment 2. In FIG. 13, the same reference signs are provided to the same components as those in FIGS. 2 and 3.

Probe 12 illustrated in FIG. 13 includes electrode 22 similarly to probe 12 described in Embodiment 1. Probe 12 includes reagent layer 23 (not illustrated in FIG. 13), reference layer 24 (not illustrated in FIG. 13), and counter electrode 22*c*, a part of which is exposed in a first surface (not illustrated in FIG. 13) similarly to probe 12 described in Embodiment 1.

The surface of probe 12 on the side on which reagent layer 23 and reference layer 24 are formed may be referred to as a first surface. The surface facing the first surface may be referred to as a second surface. The direction from the second surface to the first surface (the direction of arrow X2*a* in FIG. 13) may be referred to as a height direction.

Also, a surface that connects the first surface to the second surface and extends in the insertion direction (the direction of arrow X2 in FIG. 13) of probe 12, which is the right side surface when seen from the distal end of probe 12, may be referred to as a third surface. A surface that connects the first surface to the second surface and extends in the insertion direction of probe 12, which is the left side surface when seen from the distal end of probe 12, may be referred to as a fourth surface. Also, the surface of the distal end of probe 12 facing the insertion direction may be referred to as a distal end surface.

Note that the first surface may also be referred to as an upper surface. The second surface may also be referred to as a bottom surface. The third surface and the fourth surface may also be referred to as side surfaces.

Figure 14:
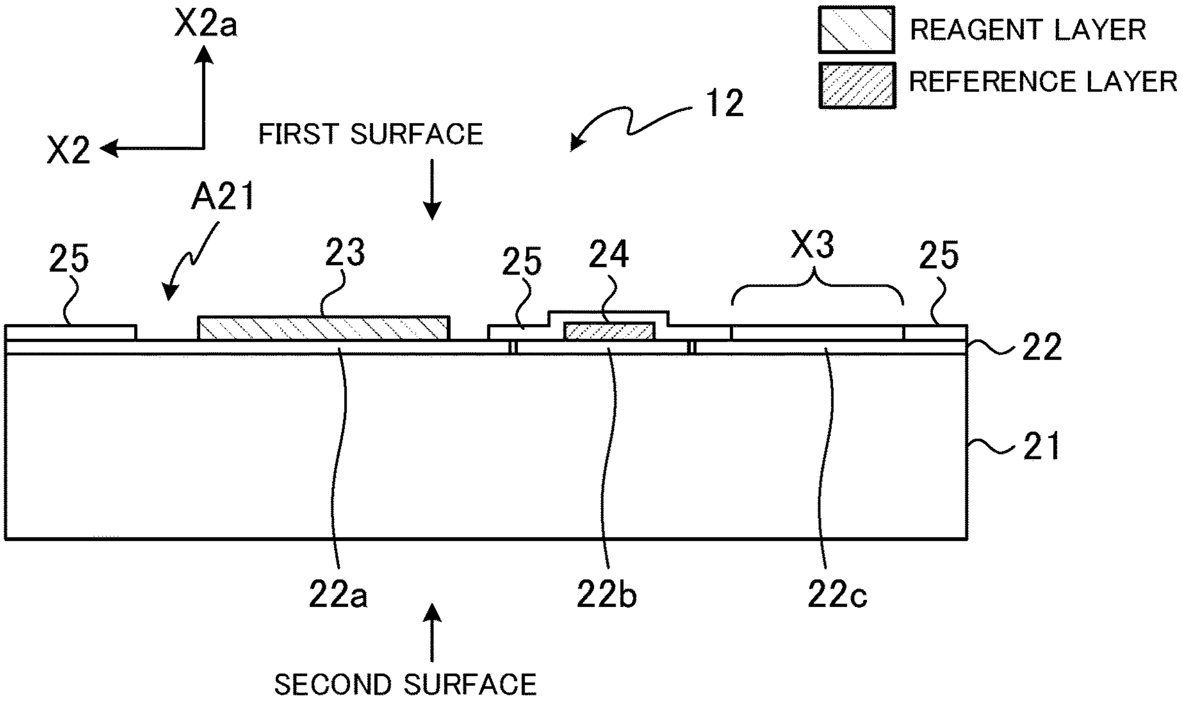
FIG. 14 illustrates a partial side view of the probe in FIG. 13 when seen from a third surface side.

FIG. 14 illustrates a partial side view of probe 12 in FIG. 13 when seen from the third surface side. FIG. 14 illustrates probe 12 before a protective film, which will be described later, is formed. As illustrated in FIG. 14, electrode 22 is formed on the first surface side of substrate 21. Electrode 22 includes working electrode 22*a*, reference electrode 22*b*, and counter electrode 22*c*.

Reagent layer 23 is formed on working electrode 22*a* of electrode 22 on the first surface side. Reference layer 24 is formed on reference electrode 22*b* of electrode 22 on the first surface side. Reference layer 24 is formed by hardening an Ag/AgCl paste applied to reference electrode 22*b*.

Working electrode 22*a* at the distal end portion of probe 12 (working electrode 22*a* on the distal end side of probe 12 with reagent layer 23 as a boundary) is covered with film 25. Note that although film 25 covering working electrode 22*a* at the distal end portion of probe 12 is in contact with reagent layer 23 in Embodiment 1, film 25 may be separated therefrom as illustrated by arrow A21 in FIG. 14.

Film 25 has an opening at a part corresponding to reagent layer 23. In this manner, reagent layer 23 on the first surface side is exposed.

Reference layer 24 on the side of the first surface is covered with film 25. In other words, reference layer 24 on the first surface side is not exposed. Reference layer 24 is exposed on the third surface side of probe 12. In other words, reference layer 24 is exposed in the width direction (the direction that is orthogonal to the insertion direction illustrated by arrow X2) of probe 12 (see FIG. 4B as well).

Film 25 has an opening such that the part in region X3 of counter electrode 22*c* on the first surface side is exposed. The opening of film 25 has a notch shape (see region X3 in (B) of FIG. 3 as well). Counter electrode 22*c* is partially exposed in the upper surface by the notch shape.

Note that the part corresponding to working electrode 22*a* from the head portion (the part in region X1 in FIG. 13) of probe 12 to reagent layer 23 may be referred to as a lead or a working electrode lead. The part corresponding to reference electrode 22*b* from the head portion of probe 12 to reference layer 24 may be referred to as a lead or a reference electrode lead. The part corresponding to counter electrode 22*c* from the head portion of probe 12 to the opening (region X3) of film 25 may be referred to as a lead or a counter electrode lead.

Also, reference layer 24 may be exposed on the fourth surface side. Reference layer 24 and counter electrode 22*c* may be formed on the second surface side. In the case in which reference layer 24 and counter electrode 22*c* are formed on the second surface side, the reference electrode lead and the counter electrode lead are formed on the second surface side.

As methods for manufacturing probe 12 (sensor 1), there are a film attachment technique and an application technique.

1. Concerning Film Attachment Technique

1a. Configuration of Probe 12

Figure 15:
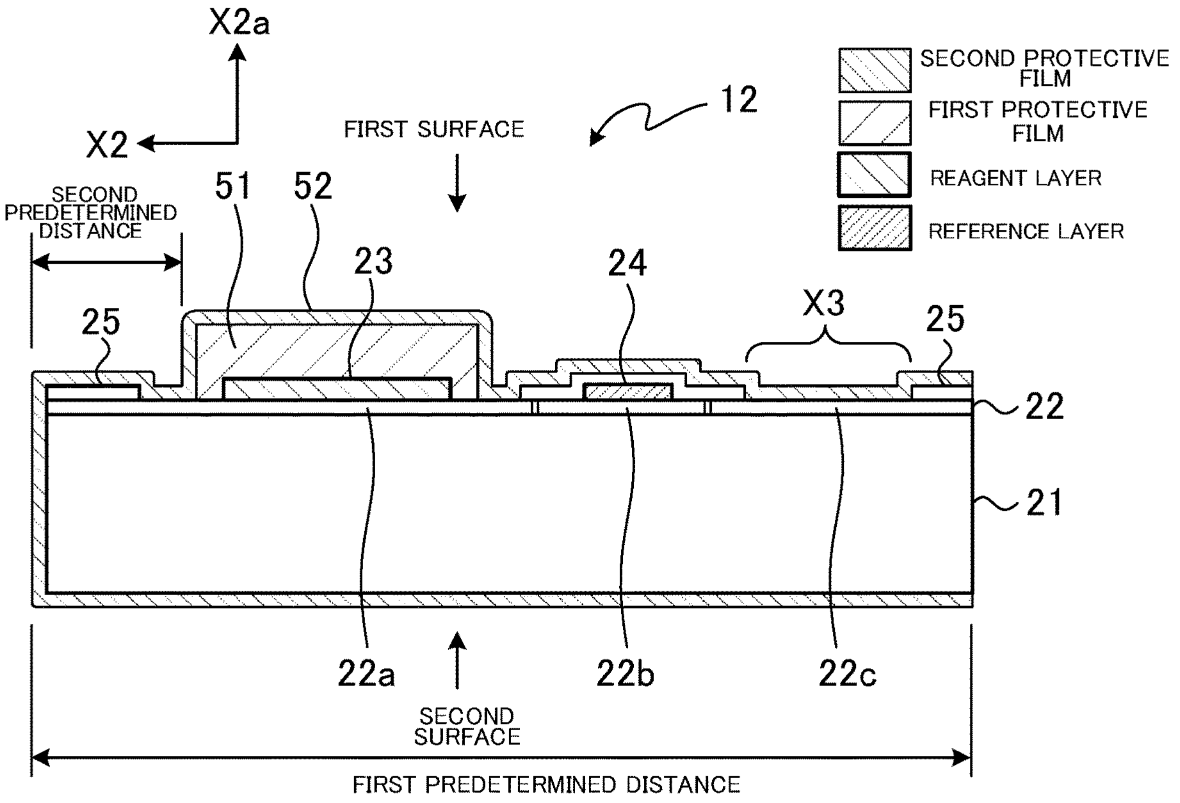
FIG. 15 illustrates a partial side view of the probe with protective films formed thereon when seen from the third surface side.

FIG. 15 illustrates a partial side view of probe 12 with protective films formed thereon when seen from the third surface side. In FIG. 15, first protective film 51 and second protective film 52 are formed for probe 12 in FIG. 14. Hereinafter, first protective film 51 and second protective film 52 may simply be referred to as protective films when they are not distinguished from each other.

First protective film 51 is formed to cover reagent layer 23 formed on working electrode 22*a*. For example, first protective film 51 is formed to cover the first surface side, the third surface side, the fourth surface side, the distal end surface side, and the side of the surface on the side opposite to the distal end surface side of reagent layer 23.

Second protective film 52 is formed to cover electrode 22, reagent layer 23, reference layer 24, and film 25 formed on substrate 21 (for example, to cover the distal end part of probe 12 illustrated in FIG. 14).

For example, second protective film 52 is formed to cover at least film 25 disposed on working electrode 22*a*, reagent layer 23 and first protective film 51 formed on working electrode 22*a*, reference layer 24 and film 25 disposed on reference electrode 22*b*, and film 25 disposed on counter electrode 22*c* and having an opening, from the distal end of probe 12.

In other words, second protective film 52 is formed to cover the part from the distal end of probe 12 to a first predetermined distance beyond at least region X3. Second protective film 52 may be formed on the first surface side, the second surface side, the third surface side, the fourth surface side, and the distal end surface side of probe 12.

Reagent layer 23 is formed at a position separated from the end of probe 12 in the insertion direction into the living body by a predetermined distance. For example, reagent layer 23 is formed from a position separated from the distal end of probe 12 by a second distance as illustrated in FIG. 15.

Counter electrode 22*c* exposed from reference layer 24 and the opening (region X3) of film 25 is formed in a region on the side opposite to the distal end side of probe 12 from reagent layer 23 as a boundary.

First protective film 51 is formed by a method of manufacturing a sensor, which will be described later. First protective film 51 is formed by a film, which is formed of a protective film material, being disposed to cover reagent layer 23.

First protective film 51 is not disposed in a second predetermined distance from the distal end of probe 12. This is for minimizing the thickness of the distal end portion of probe 12 in consideration of easiness of insertion of probe 12 into the living body. Also, this is because there is a concern that first protective film 51 may be dissociated at the time of the insertion into the living body if first protective film 51 (including reagent layer 23) is disposed at the distal end of probe 12.

First protective film 51 is thicker than second protective film. For example, the thickness of first protective film 51 (the thickness of first protective film 51 does not include the thickness of second protective film 52 disposed on first protective film 51) is thicker than the second protective film disposed on the first surface corresponding to the second predetermined distance in the height direction of probe 12.

Since it is necessary for first protective film 51 and second protective film 52 to transmit the analyte that is present outside the protective films into the protective films while preventing or curbing leakage of substances (mainly oxidoreductase) contained in reagent layer 23 to the outside of the protective films, it is only necessary for these protective films to have holes with a size with which the analyte can be sufficiently transmitted therethrough and oxidoreductase cannot be transmitted therethrough or is unlikely to be transmitted therethrough, and the protective films may be made of the same material or different materials.

Figure 16:
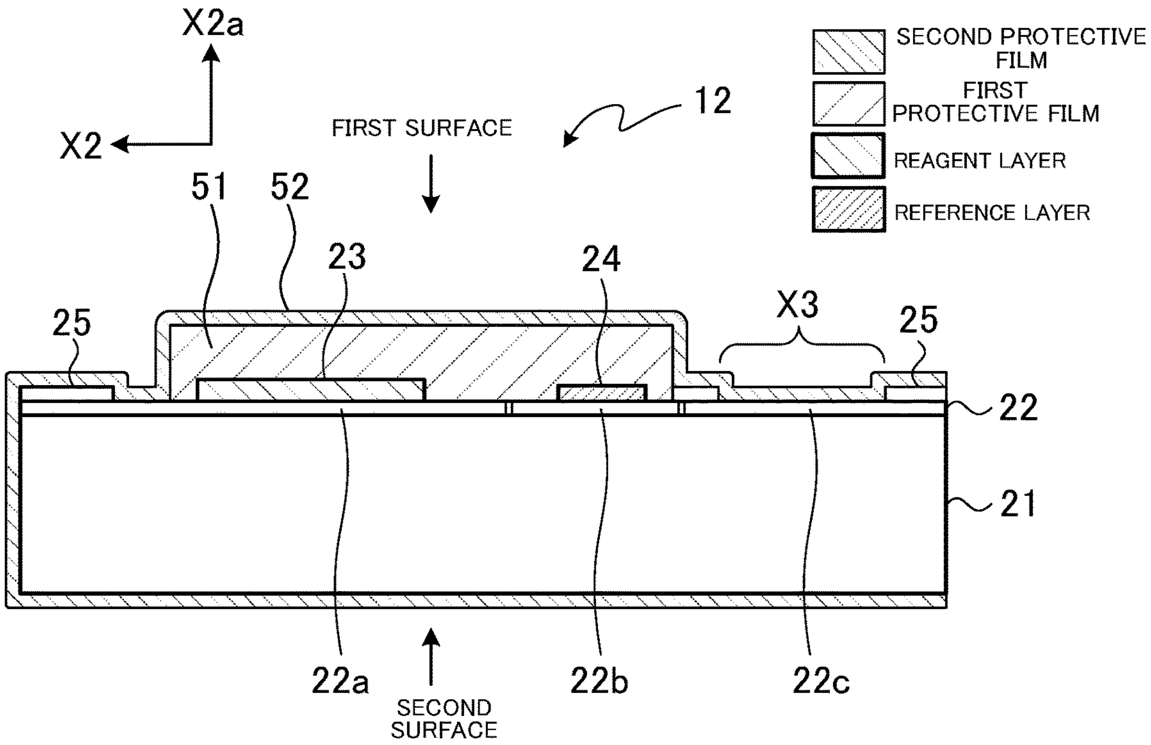
FIG. 16 illustrates a partial side view of the probe with the protective films formed thereon when seen from the third surface side.

First protective film 51 may cover working electrode 22*a* including reagent layer 23 as illustrated in FIG. 15 or may also cover reference layer 24 as illustrated in FIG. 16.

FIG. 16 is a partial side view of probe 12 with protective films formed thereon when seen from the third surface side. In FIG. 16, the same reference signs are provided to the same components as those in FIG. 15. As illustrated in FIG. 16, first protective film 51 may also cover reference layer 24. In the case in which reference layer 24 is covered with first protective film 51, film 25 may not be disposed on the upper surface of reference layer 24.

Note that although not illustrated in the drawing, first protective film 51 may also cover counter electrode 22*c* (counter electrode 22*c* at the part corresponding to region X3) exposed from film 25. However, in the case in which reference layer 24 or counter electrode 22*c* is covered, reference electrode 22*b* or counter electrode 22*c* is disposed on the same surface as that of working electrode 22*a*.

1b. Method for Manufacturing Probe 12

Hereinafter, an example of a method for manufacturing probe 12 in a case in which poly(tert-butyl methacrylate-b-poly(4-vinylpyridine) (hereinafter, referred to as tBuMA4VP) is used for a protective film will be described.

FIGS. 17A to 17D describes the example of a method for manufacturing probe 12.

(Process A)

In Process A, a protective film sheet as a base of first protective film 51 is formed. The protective film sheet may be referred to as a protective film.

First, tBuMA4VP that is a protective film material and poly(ethylene glycol)diglycidyl ether (hereinafter, referred to as PEGDGE) that is a crosslinking agent are dissolved in ethanol and prepared such that the final concentrations thereof are 8% and 0.62%, respectively (the solution is used as the protective film solution).

Figure 17A:
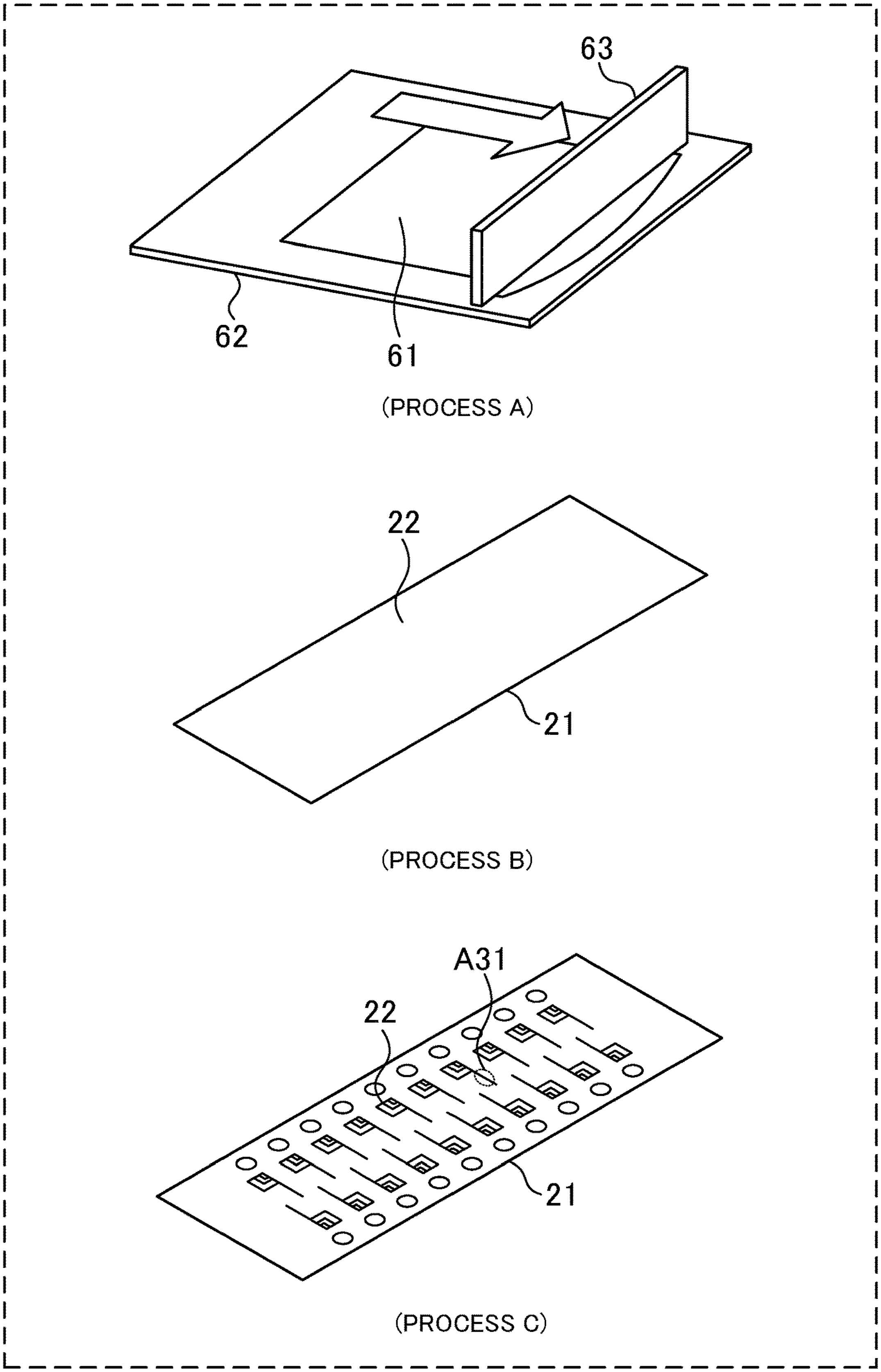
FIG. 17A describes an example of a method for manufacturing the probe.

As illustrated in (Process A) in FIG. 17A, protective film solution 61 is uniformly applied and spread on base material sheet 62 using squeegee 63 and is then dried. In other words, the protective film as a base of first protective film 51 is formed on base material sheet 62.

The thickness of the protective film formed on the base material sheet may be 20 μm, for example. In a case in which the predetermined thickness is not achieved by performing the application and the spreading once, overcoating may be performed a plurality of times.

After the protective film with a predetermined thickness is formed, the base material sheet is cut into a shape having substantially the same diameter as an opening diameter (for example, 03.5 mm) in Process H, which will be described later.

Note that the thickness of the protective film formed on the base material sheet may fall within a range of equal to or greater than 5 μm and equal to or less than 60 μm. The thickness preferably falls within a range of equal to or greater than 10 μm and equal to or less than 45 μm and more preferably falls within a range of equal to or greater than 20 μm and equal to or less than 40 μm.

It is desirable that the concentration of the protective film component and the concentration of the crosslinking agent in the protective film solution be weight percentages (w/v %) of equal to or greater than ¼ and equal to or less than ½ the dissolution limit concentration of the protective film component with respect to the solvent for dissolution.

For example, since the dissolution limit concentration of tBuMA4VP with respect to ethanol is about 20%, the concentration is preferably equal to or greater than 5 w/v % and equal to or less than 10 w/n %. Also, since the PEDGE concentration for the crosslinking agent be equal to or greater than 0.39 w/v % and equal to or less than 0.78% w/v since the dissolution limit with respect to ethanol is about 1.55%.

Although ethanol is adopted in Process A and Process J, which will be described later, as the organic solvent for dissolution, the organic solvent for dissolution is not particularly limited as long as it can dissolve the protective film solution and does not have any influences (such as leading a great decrease in enzyme activity) of oxidoreductase to be used. However, the organic solvent for dissolution is preferably alcohol solvents. Among the alcohol solvents, lower alcohol solvents (the number of carbon chains is equal to or less than 6) are preferably used, and examples thereof other than ethanol include methanol and isopropyl alcohol. A plurality of types of these organic solvents may be used in combination.

(Process B)

As illustrated in (Process B) in FIG. 17A, electrode 22 is formed on substrate 21 on the sheet. For example, an electrode material such as gold is sputtered on sheet-shaped substrate 21 such as polyethylene terephthalate (PET) to form electrode 22.

(Process C)

As illustrated in (Process C) in FIG. 17A, working electrode 22*a*, reference electrode 22*b*, and counter electrode 22*c* are formed. For example, laser working is used to form working electrode 22*a*, reference electrode 22*b*, and counter electrode 22*c*. In (Process C) in FIG. 17A, an example in which working electrode 22*a*, reference electrode 22*b*, and counter electrode 22*c* are formed on one surface is illustrated.

(Process D)

Figure 17B:
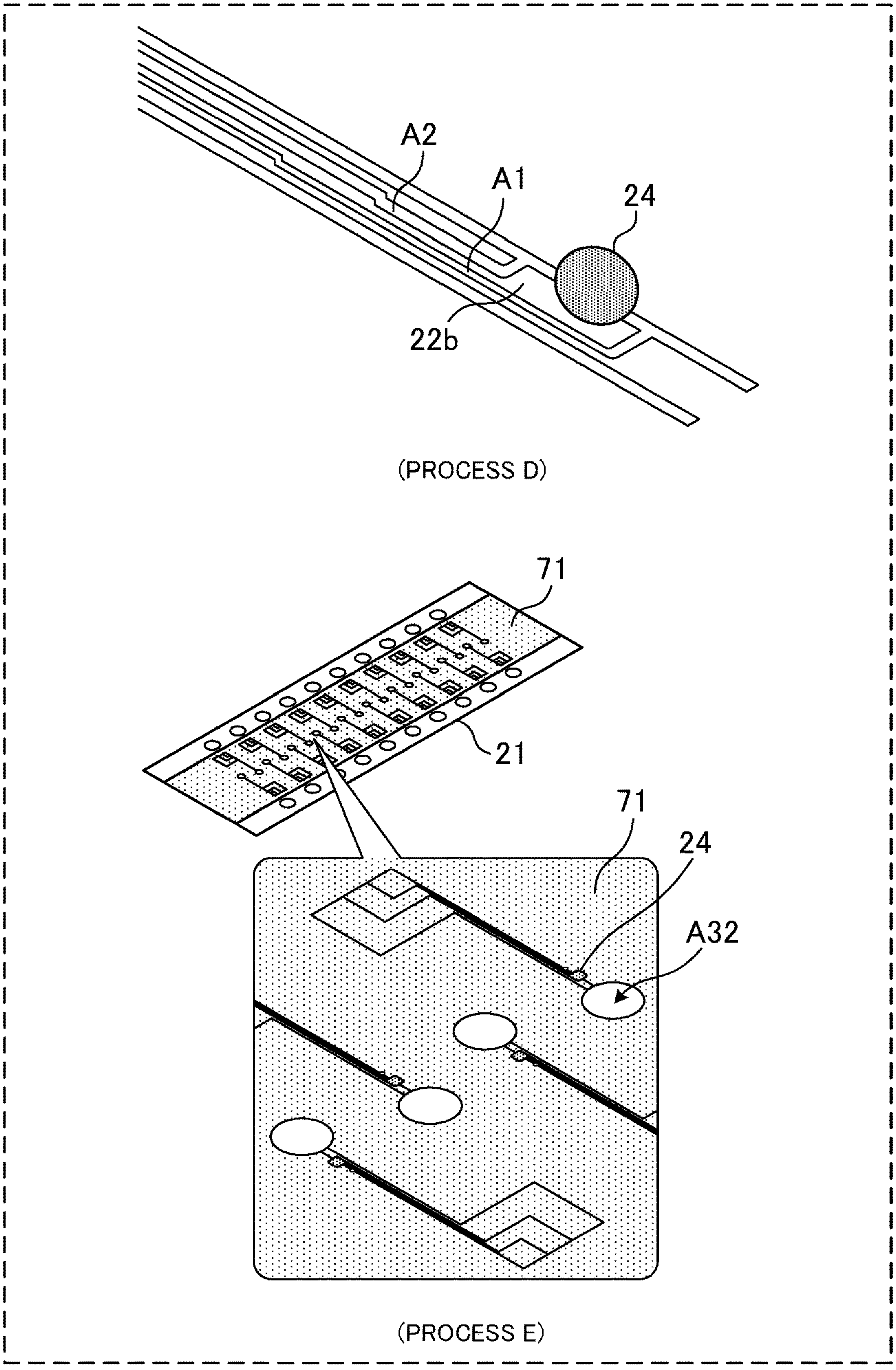
FIG. 17B describes the example of the method for manufacturing the probe.

As illustrated in (Process D) in FIG. 17B, reference layer 24 is formed on reference electrode 22*b*. For example, an Ag/AgCl paste is applied to reference electrode 22*b* and is then dried thereby to form reference layer 24. At that time, the Ag/AgCl paste is disposed to cross over reference electrode 22*b* and the part corresponding to the outside of probe 12 (the part separated from probe 12).

Note that (Process D) in FIG. 17B is an enlarged view of dashed line frame A31 part in (Process C) in FIG. 17A. In (Process D) in FIG. 17B, reference electrode 22*b*, grooves A1 and A2, and the Ag/AgCl paste formed on substrate 21 are illustrated. In (Process D) in FIG. 17B, illustration of the head portion, reagent layer 23, and film 25 of probe 12 is omitted.

(Process E)

As illustrated in (Process E) in FIG. 17B, first film 71 (a film that is different from film 25) is attached to sheet-shaped substrate 21. First film 71 has openings at a part where reagent layer 23 is formed and a part where counter electrode 22*c* is exposed (the part corresponding to region X3 illustrated in FIG. 14, for example).

Hereinafter, the opening at the part where reagent layer 23 is formed in first film 71 and film 25 may be referred to as a first opening. The opening at the part where counter electrode 22*c* in first film 71 and film 25 may be referred to as a second opening. Note that arrow A32 in (Process E) in FIG. 17B illustrates the first opening in first film 71. Illustration of the second opening in first film 71 is omitted.

In regard to First film 71, the contact angle with the liquid on first film 71 is preferably greater than the contact angle with the liquid at the opening, and a greater difference therebetween is more preferable, in terms of application of the reagent, for example.

The diameter of the first opening in first film 71 may be 2.5 mm, for example. Also, the second opening may not be formed in first film 71.

(Process F)

Figure 17C:
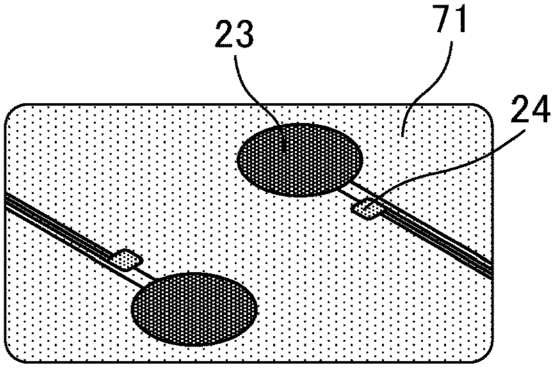
FIG. 17C describes the example of the method for manufacturing the probe.
Figure 17C:
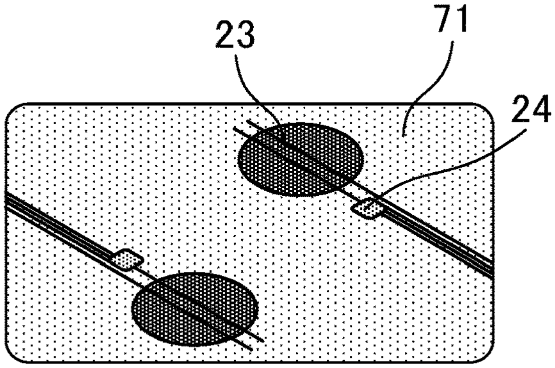
Figure 17C:
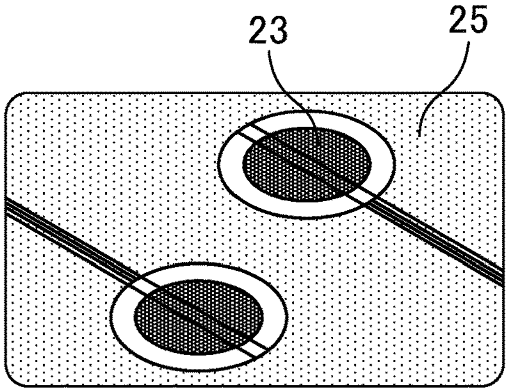

As illustrated in (Process F) in FIG. 17C, a reagent solution is applied to the first opening in first film 71 attached to sheet-shaped substrate 21 to form reagent layer 23.

(Process G)

As illustrated in (Process G) in FIG. 17C, reagent layer 23 and the electrode material part (working electrode 22*a*) are trimmed (see Embodiment 1 for the trimming). Note that the trimming (Process G) may not be performed for probe 12 in Embodiment 2.

(Process H)

First film 71 attached in Process E is peeled off from substrate 21. Then, film 25 having the first opening and the second opening is attached to sheet-shaped substrate 21 as illustrated in (Process H) in FIG. 17C. The first opening in film 25 is located at the part corresponding to reagent layer 23, and the second opening is located at the part corresponding to region X3 in counter electrode 22*c*. The upper surface of reference layer 24 is covered with film 25. In (Process H) in FIG. 17C, illustration of the second opening in film 25 is omitted.

Note that the diameter of the first opening in film 25 may be greater than the first opening in first film 71 and may be, for example, 3.5 mm. In other words, the first opening in film 25 may have a size with which it surrounds reagent layer 23.

(Process I)

Figure 17D:
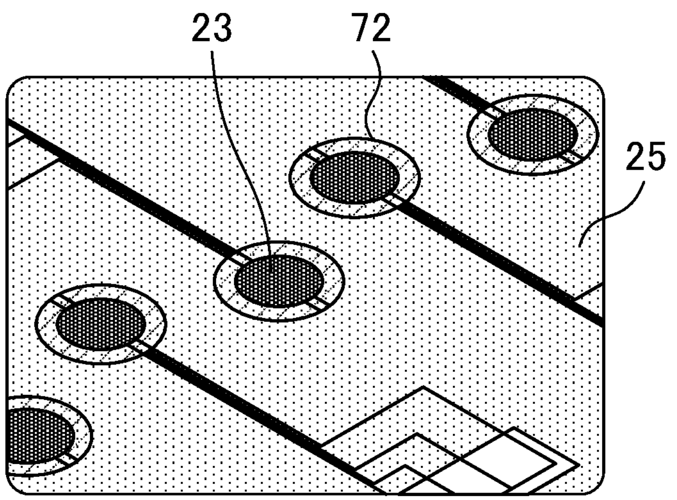
FIG. 17D describes the example of the method for manufacturing the probe.
Figure 17D:
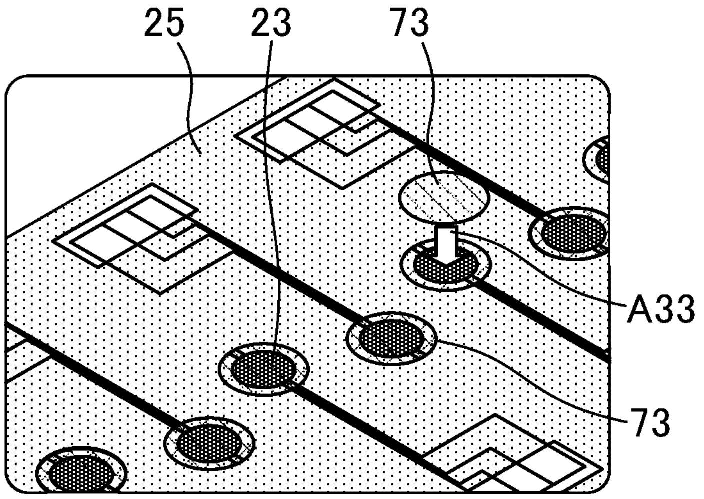

As illustrated in (Process I) in FIG. 17D, ethanol 72 is applied to the first opening in film 25. For example, an amount of ethanol 72 for covering the first opening is applied. If the diameter of the first opening is assumed to be 3.5 mm, about 3 ul or more and about 5 ul or less of ethanol 72 is applied thereto.

Note that for film 25, a material of film 25 is preferably selected such that a contact angle formed between the liquid (ethanol 72 in this case) that is in contact with film 25 and film 25 is greater than the contact angle formed with the liquid (ethanol 72 in this case) in the first opening in a case in which these contact angles are compared. This is for retaining the applied liquid (ethanol 72 in this case) in the first opening such that the liquid does not leak from the first opening. Also, the difference between both the contact angles is preferably greater. The difference between both the contact angles is preferably equal to or greater than 20°, is more preferably equal to or greater than 35°, and is further preferably equal to or greater than 50°, for example.

(Process J)

As illustrated in (Process J) in FIG. 17D, protective film sheet 73 formed and cut in Process A is disposed (placed) at the first opening in film 25 as illustrated by arrow A33. Then, ethanol 72 applied in Process I is dried. Since protective film sheet 73 is thus dried while being partially dissolved by ethanol 72, it is possible to form first protective film 51 that tightly adheres to reagent layer 23.

(Process K)

Figure 17E:
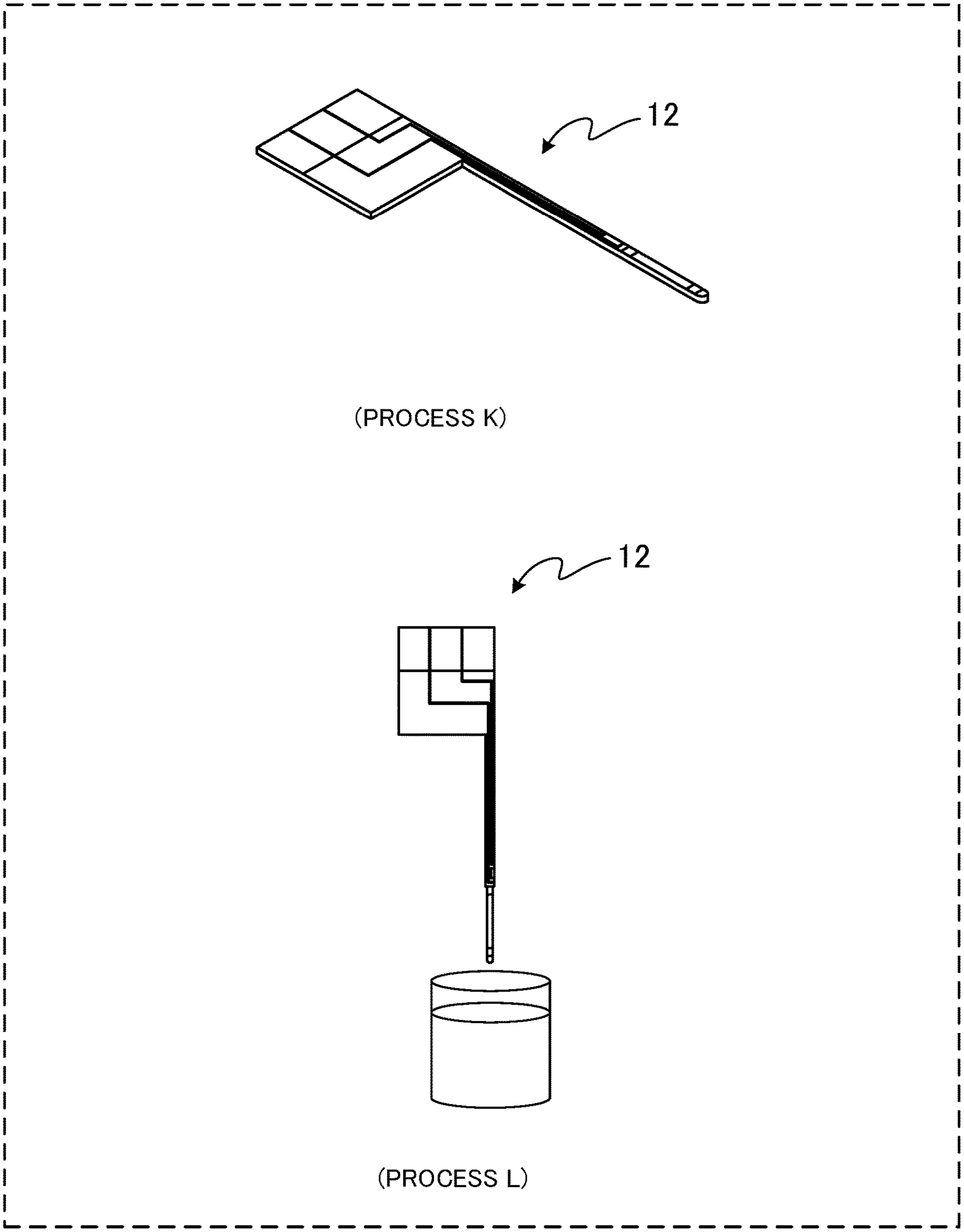
FIG. 17E describes the example of the method for manufacturing the probe.

As illustrated in (Process K) in FIG. 17E, sheet-shaped substrate 21 is cut into the shape of probe 12.

(Process L)

As illustrated in (Process L) in FIG. 17E, cut probe 12 is dipped into a protective film solution with the same composition as that in Process A (the composition may be different) and is then dried. The dipping and the drying may be repeated any number of times from one to three, for example. Second protective film 52 is thus formed on probe 12.

The thickness of second protective film 52 is preferably set within a range of equal to or greater than 5% and equal to or less than 60% of the thickness of first protective film 51. Also, the thickness of second protective film 52 is more preferably set within a range of equal to or greater than 10% and equal to or less than 50% and is further preferably set within a range of equal to or greater than 20% and equal to or less than 40%.

In a case in which the same protective film solution as that in Process A is adopted as the protective film solution into which probe 12 is dipped, it is possible to form second protective film 52 with a thickness of equal to or greater than 1 μm and equal to or less than 4 μm through one-time dipping, with a thickness of equal to or greater than 2 μm and equal to or less than 8 μm through two-time dipping, and with a thickness of equal to or greater than 3 μm and equal to or less than 12 μm through three-time dipping.

2. Concerning Application Technique

2a. Configuration of Probe 12

Probe 12 manufactured by application technique also has basically the same configuration as that of probe 12 manufactured by the film attachment technique. Hereinafter, differences in the configurations will be described.

Figure 18:
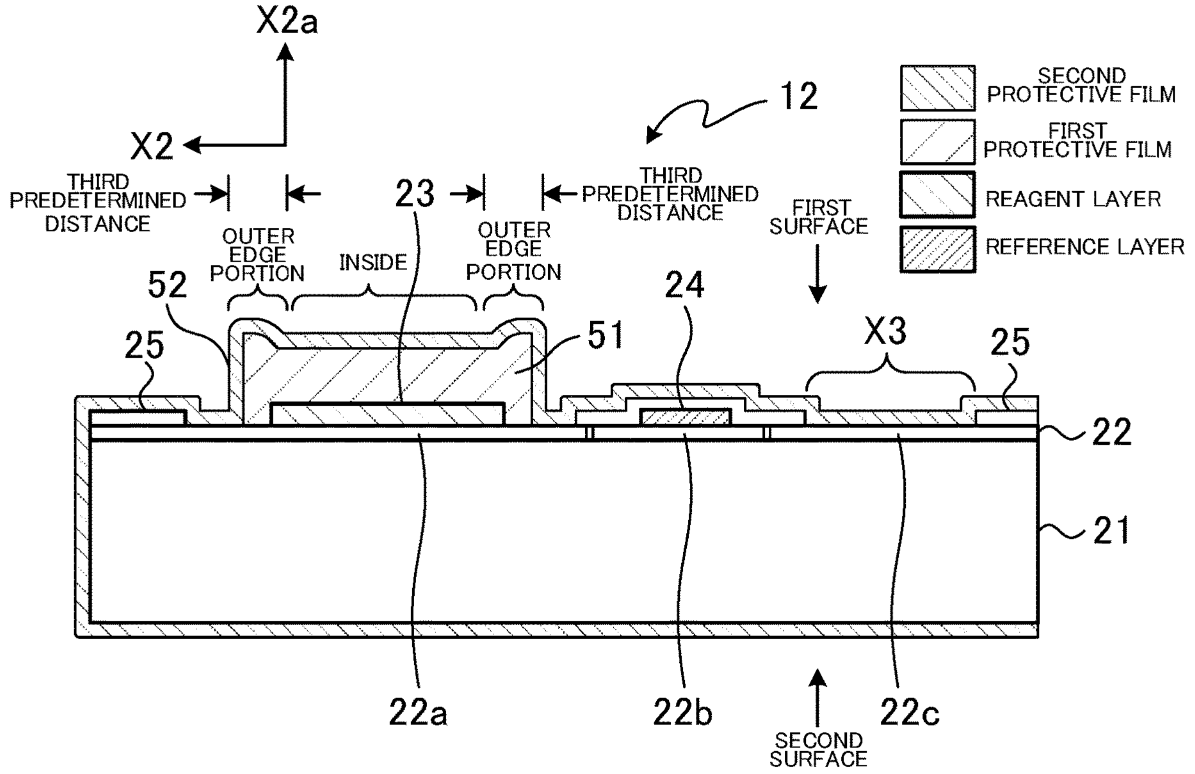
FIG. 18 illustrates a partial side view of the probe with the protective films formed thereon when seen from the third surface side.
Figure 19:
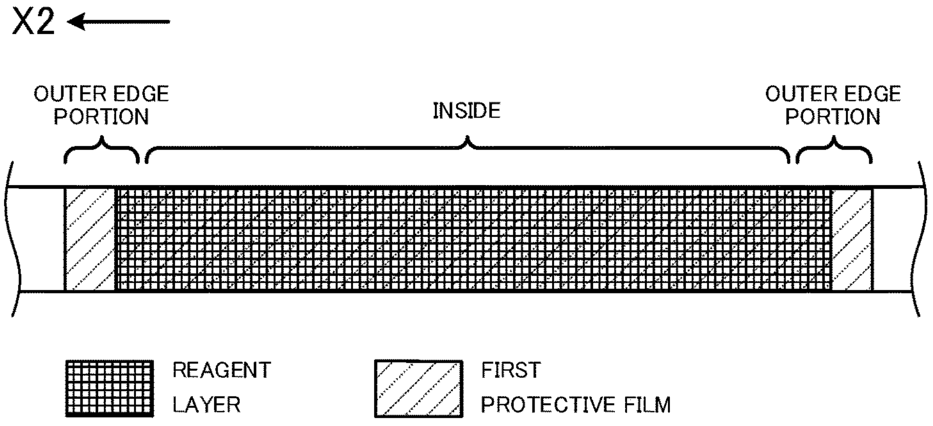
FIG. 19 illustrates a top view of a distal end part of the probe in FIG. 18.

FIG. 18 illustrates a partial side view of probe 12 with protective films formed thereon when seen from the third surface side. FIG. 19 illustrates a top view of the distal end part of probe 12 in FIG. 18. In the application technique, the shape of first protective film 51 is different from the shape of first protective film 51 (see FIG. 15, for example) formed by the film attachment technique.

As illustrated in FIGS. 18 and 19, first protective film 51 formed by the application technique has raised both ends in the direction along the insertion direction of probe 12 into the living body. In other words, first protective film 51 has a projecting shape at both ends in the insertion direction of probe 12 into the living body.

Hereinafter, the raised parts of first protective film 51 may be referred to as an outer edge portions. The width of the outer edge portions has a third predetermined distance as illustrated in FIG. 18. Also, the region interposed between the outer edge portions of first protective film 51 may be referred to as inside.

As will be described below in the method for manufacturing probe 12, the protective film solution is dropped onto the part corresponding to reagent layer 23 and is then dried thereby to form first protective film 51 in the application technique. Since a coffee ring is formed at the outer edge portions when the protective film solution is dried, the outer edge portion (raised parts) are formed in first protective film 51. The outer edge portions are parts corresponding to the coffee ring, and the inside can be regarded as corresponding to the part other than the coffee ring.

Note that the outer edge portions in the direction along the insertion direction of probe 12 is cut (removed) from probe 12 by the cutting of substrate 21, which will be described later in the method for manufacturing probe 12. On the other hand, in a case in which first protective film 51 is formed into a circular shape, for example, on working electrode 22*a* that is not cut from probe 12 (in other words, on working electrode 22*a* remaining in probe 12 after the cutting), a circular coffee ring (outer edge portion) is formed. In other words, the outer edge portion of first protective film 51 is included at least at both ends in the insertion direction of probe 12 into the living body.

Figure 20:
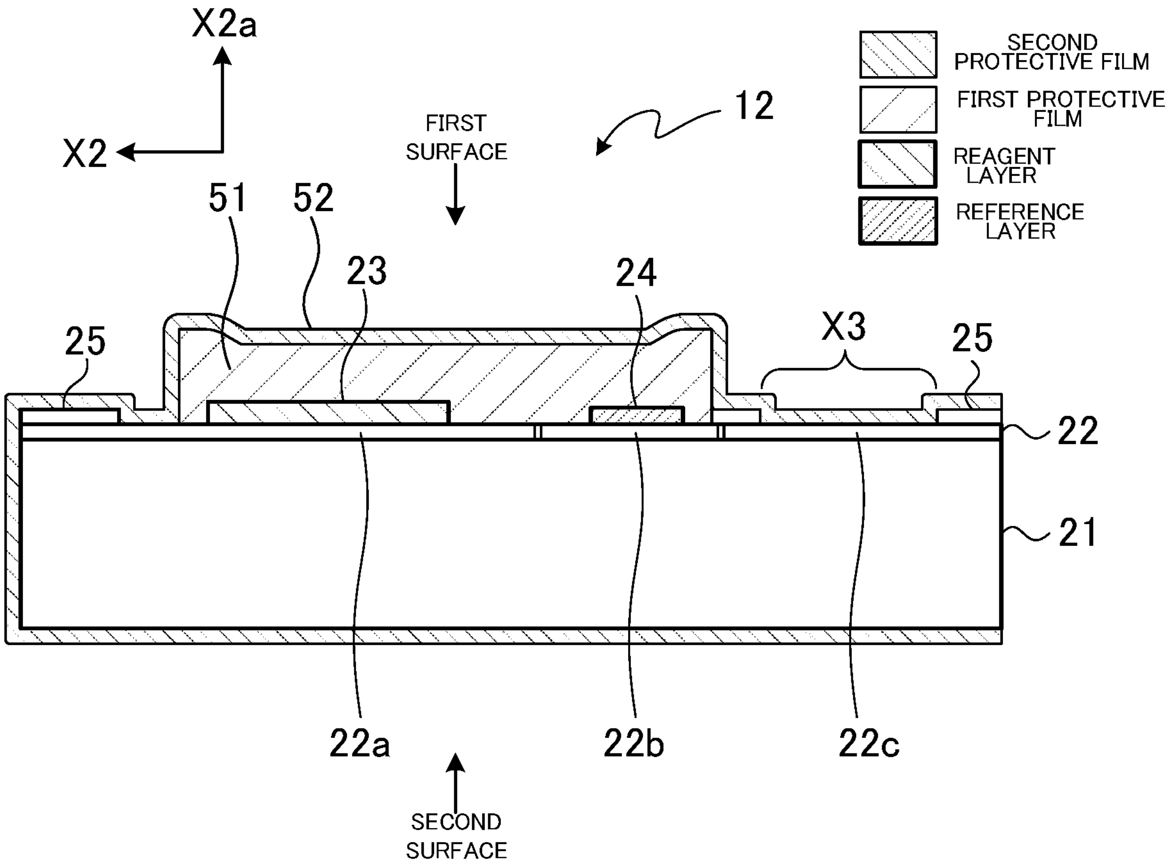
FIG. 20 illustrates a partial side view of the probe with the protective films formed thereon when seen from the third surface side.

First protective film 51 may cover working electrode 22*a* including reagent layer 23 as illustrated in FIG. 18 or may also cover reference layer 24 as illustrated in FIG. 20.

FIG. 20 is a partial side view of probe 12 with protective films formed thereon when seen from the third surface side. In FIG. 20, the same reference signs are provided to the same components as those in FIG. 18. As illustrated in FIG. 20, first protective film 51 may also cover reference layer 24.

In the case in which reference layer 24 is covered with first protective film 51, film 25 may not be disposed on the upper surface of reference layer 24.

Although not illustrated in the drawing, first protective film 51 may also cover counter electrode 22*c* (counter electrode 22*c* at the part corresponding to region X3) exposed from film 25. However, in the case in which reference layer 24 or counter electrode 22*c* is covered, reference electrode 22*b* or counter electrode 22*c* are placed on the same surface as that of working electrode 22*a*.

2b. Method for Manufacturing Probe 12

Hereinafter, an example of a method for manufacturing probe 12 in a case in which tBuMA4VP is used as a living body protective film will be described below.

FIGS. 21A to 21D describe the example of the method for manufacturing probe 12.

(Process A)

Figure 21A:
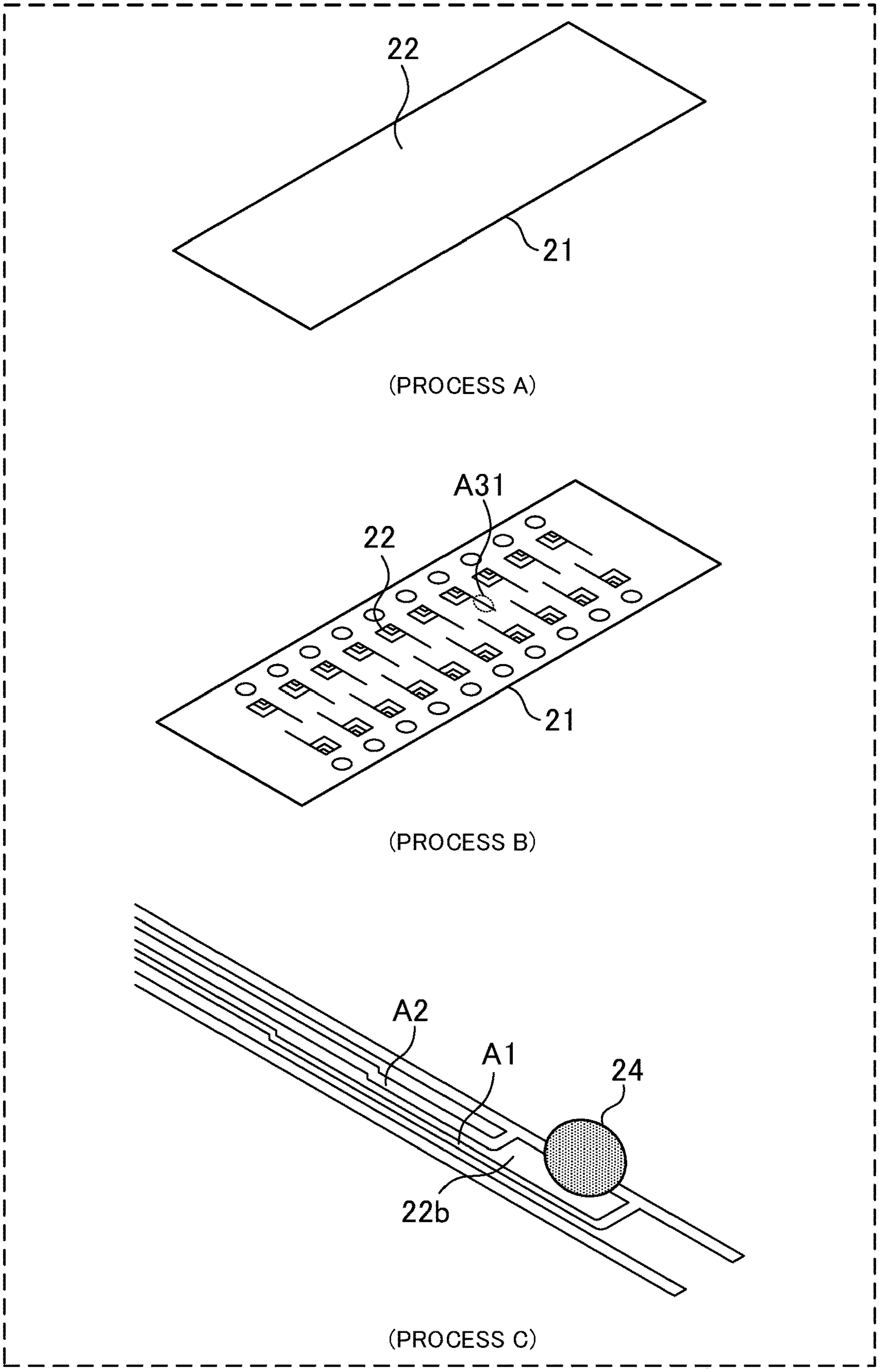
FIG. 21A describes an example of a method for manufacturing the probe.

As illustrated in (Process A) in FIG. 21A, electrode 22 is formed on substrate 21 on a sheet. For example, an electrode material such as gold is sputtered on sheet-shaped substrate 21 such as polyethylene terephthalate (PET) to form electrode 22.

(Process B)

As illustrated in (Process B) in FIG. 21A, working electrode 22*a*, reference electrode 22*b*, and counter electrode 22*c* are formed. For example, laser working is used to form working electrode 22*a*, reference electrode 22*b*, and counter electrode 22*c*. In (Process B) in FIG. 21A, an example in which working electrode 22*a*, reference electrode 22*b*, and counter electrode 22*c* are formed on one surface is illustrated.

(Process C)

As illustrated in (Process C) in FIG. 21A, reference layer 24 is formed on reference electrode 22*b*. For example, an Ag/AgCl paste is applied to reference electrode 22*b* and is then dried to form reference layer 24. At that time, the Ag/AgCl paste is placed to cross over reference electrode 22*b* and the part corresponding to the outside of probe 12 (the part cut from probe 12) when substrate 21 is cut in cutting processing in Process K, which will be described later.

(Process D)

Figure 21B:
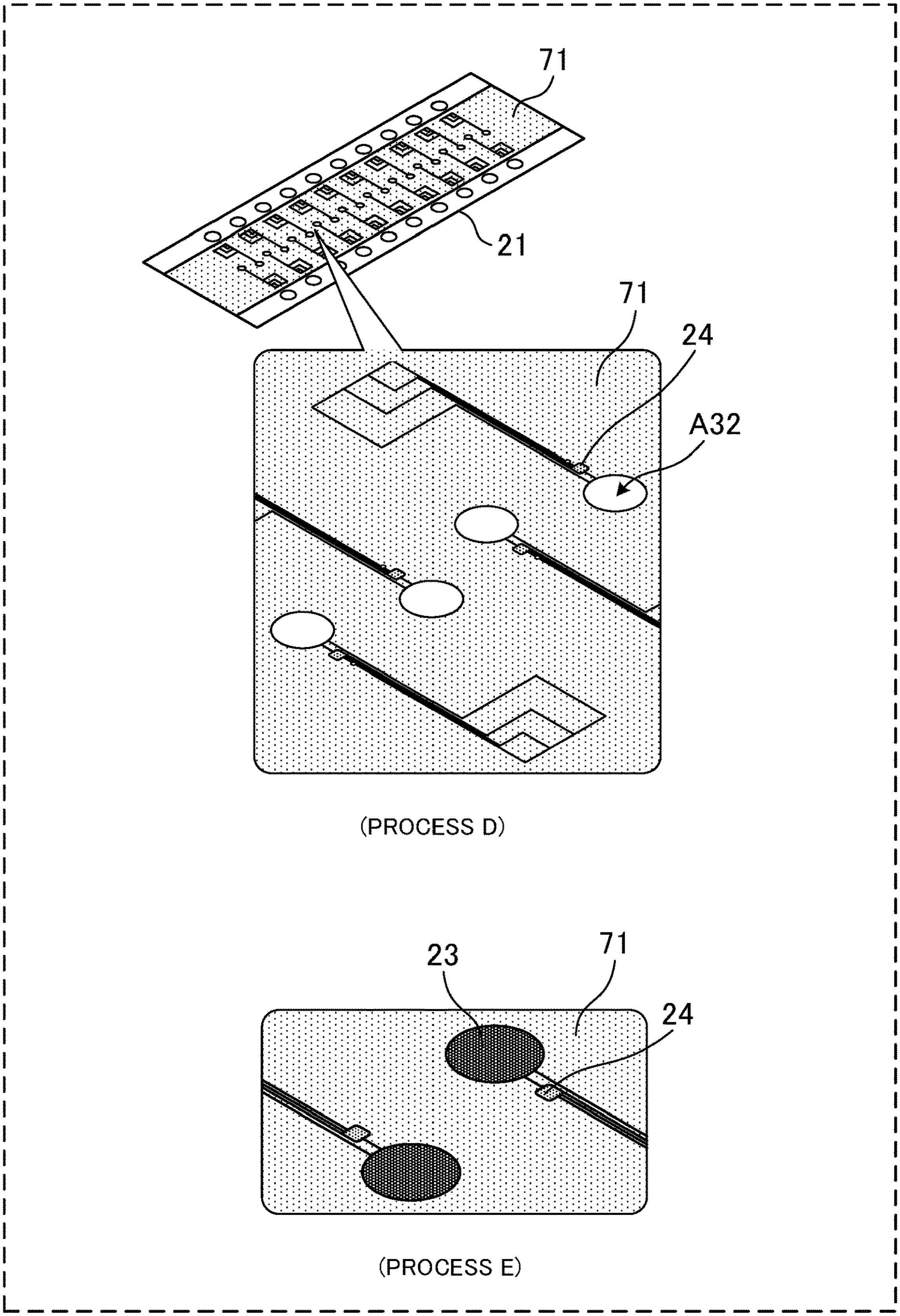
FIG. 21B describes the example of the method for manufacturing the probe.

As illustrated in (Process D) in FIG. 21B, first film 71 (a film that is different from film 25) is attached to sheet-shaped substrate 21. First film 71 has openings in the part where reagent layer 23 is formed and the part where counter electrode 22*c* is exposed (the part corresponding to region X3 illustrated in FIG. 18, for example).

Hereinafter, the opening at the part where reagent layer 23 in first film 71 and film 25 may be referred to as a first opening. The opening at the part where counter electrode 22*c* is exposed in first film 71 and film 25 may be referred to as a second opening. Note that arrow A32 in (Process D) in FIG. 21B illustrates the first opening. Illustration of the second opening is omitted.

In regard to first film 71, the contact angle with the liquid on first film 71 is preferably greater than the contact angle with the liquid at the opening, and a greater difference therebetween is more preferable, in terms of application of the reagent, for example.

The diameter of the first opening in first film 71 may be 2.5 mm, for example. Also, the second opening may not be formed in first film 71.

(Process E)

As illustrated in (Process E) in FIG. 21B, a reagent solution is applied to the first opening in first film 71 attached to sheet-shaped substrate 21 to form reagent layer 23.

(Process F)

Figure 21C:
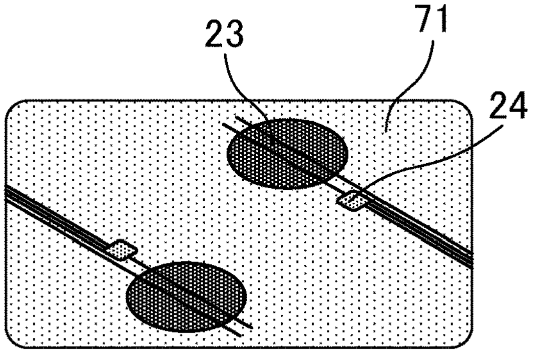
FIG. 21C describes the example of the method for manufacturing the probe.
Figure 21C:
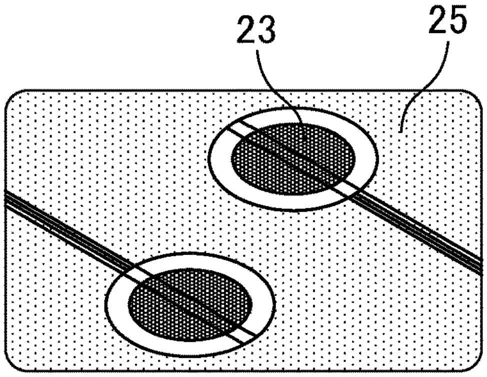
Figure 21C:
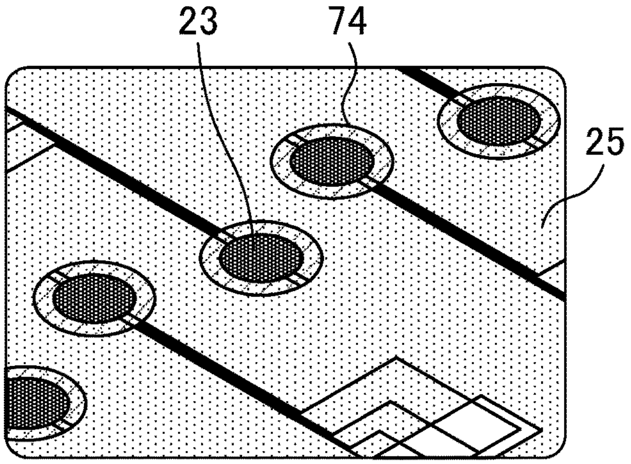

As illustrated in (Process F) in FIG. 21C, reagent layer 23 and the electrode material part (working electrode 22*a*) are trimmed (see Embodiment 1 for the trimming). Note that the trimming (Process F) may not be performed for probe 12 in Embodiment 2.

(Process G)

First film 71 attached in Process D is peeled off from substrate 21. Then, film 25 having the first opening and the second opening is attached to sheet-shaped substrate 21 as illustrated in (Process G) in FIG. 21C. The first opening in film 25 is located at the part corresponding to reagent layer 23, and the second opening is located at the part corresponding to region X3 of counter electrode 22*c*. The upper surface of reference layer 24 is covered with film 25.

Note that the diameter of the first opening in film 25 may be greater than the diameter of the first opening in first film 71 and may be 3.2 mm, for example. In other words, the diameter of the first opening in film 25 may be any size with which it surrounds reagent layer 23.

(Process H)

As illustrated in (Process H) in FIG. 21C, protective film solution 74 is applied to the first opening in film 25. For example, an amount of protective film solution 74 for covering the first opening is applied. Then, applied protective film solution 74 is dried to form first protective film 51.

Note that for film 25, a material of film 25 is preferably selected such that the contact angle formed between the liquid (protective film solution 74 in this case) that is in contact with film 25 and film 25 is greater than the contact angle formed with the liquid in the first opening (protective film solution 74 in this case) in a case in which the contact angles are compared. This is for retaining the liquid in the first opening such that the applied liquid (protective film solution 74 in this case) does not leak from the first opening. A greater difference between both the contact angles is more preferable. The difference between both the contact angles is preferably equal to or greater than 20°, is more preferably equal to or greater than 35°, and is further preferably equal to or greater than 50°, for example.

Protective film solution 74 is produced by dissolving tBuMA4VP and poly(ethylene glycol)diglycidyl ether (hereinafter, referred to as PEGDGE) that is a crosslinking agent in ethanol and preparing the mixture such that the final concentration is 8% and 0.62%, respectively.

The drying temperature may be set within a range of equal to or greater than 10° C. and equal to or less than 65° C., for example. The drying may be performed for a period of time of equal to or greater than several minutes and equal to or less than several tens of minutes, for example.

(Process I)

Figure 21D:
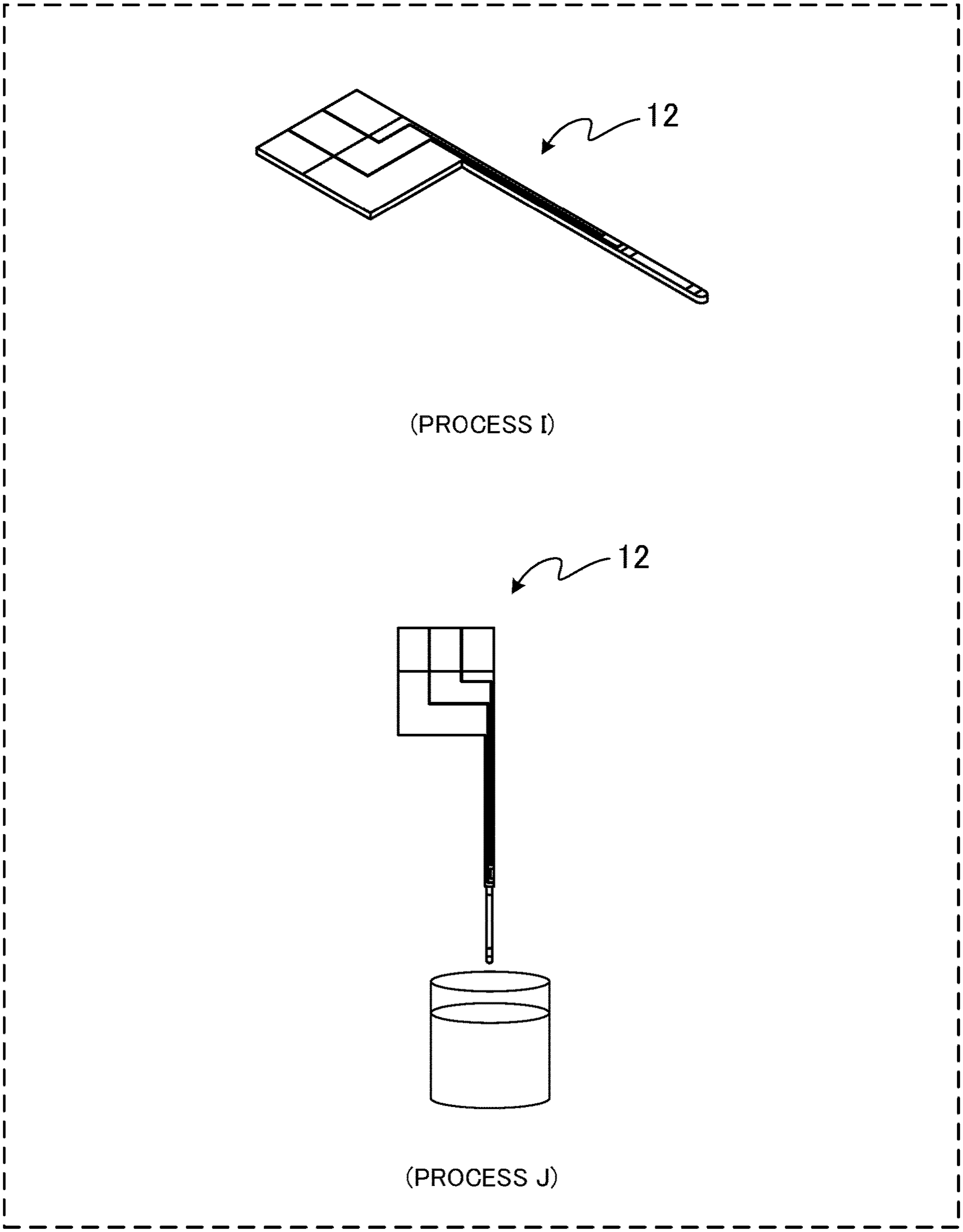
FIG. 21D describes the example of the method for manufacturing the probe.

As illustrated in (Process I) in FIG. 21D, sheet-shaped substrate 21 is cut into the shape of probe 12.

(Process J)

As illustrated in (Process J) in FIG. 21D, cut probe 12 is dipped into a protective film solution with the same composition as that in Process H (the composition may be different) and is then dried. The dipping and the drying may be repeated any number of times from one to three, for example. In this manner, second protective film 52 is formed on probe 12.

The thickness of second protective film 52 is preferably set within a range of equal to or greater than 5% and equal to or less than 60% of the thickness of first protective film 51. Also, the thickness of second protective film 52 is more preferably set within a range of equal to or greater than 10% and equal to or less than 50% and is further preferably set within a range of equal to or greater than 20% and equal to or less than 40%.

In the case in which the same protective film solution as that in Process A is adopted as the protective film solution into which probe 12 is dipped, it is possible to form second protective film 52 with a thickness of equal to or greater than 1 μm and equal to or less than 4 μm through one-time dipping, with a thickness of equal to or greater than 2 μm and equal to or less than 8 μm through two-time dipping, and with a thickness of equal to or greater than 3 μm and equal to or less than 12 μm through three-time dipping.

Figure 22:
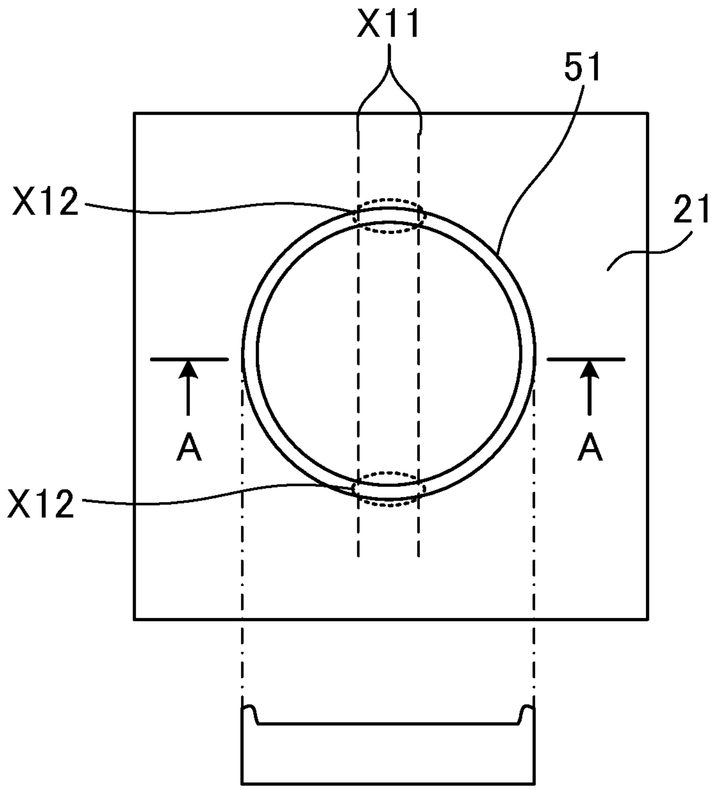
FIG. 22 describes a shape example of first protective film 51 formed in process H.

FIG. 22 describes a shape example of first protective film 51 formed in Process H. FIG. 22 illustrates a top view of first protective film 51 and a sectional view along arrow A-A. Also, dashed line X11 illustrated in FIG. 22 illustrates a cut line along which the cutting is performed in Process I.

As illustrated in FIG. 22, first protective film 51 has a circular coffee ring after Process H. The part surrounded by dashed line frame X12 in the circular coffee ring remains in probe 12 through the cutting in Process I. In other words, first protective film 51 has outer edge portions at both ends of first protective film 51 in the insertion direction of probe 12 into the living body.

As described above, probe 12 of sensor 1 that is to be inserted into the living body to measure the analyte includes substrate 21, electrode 22 that is formed on substrate 21, reagent layer 23 that is formed on electrode 22, first protective film 51 that is formed on reagent layer 23, and second protective film 52 that is thinner than first protective film 51 and is formed on first protective film 51.

In this manner, since first protective film 51 is formed on reagent layer 23, and second protective film 52 that is thinner than first protective film 51 is formed on first protective film 51, the number of processes to form the protective films of reagent layer 23 is reduced, and variations in thickness and shape of sensor 1 are reduced. Thus, sensor 1 can be easily manufactured, and variations in performance are reduced.

For example, sheet-shaped first protective film 51 with a predetermined thickness manufactured in advance is attached to the position including at least the part corresponding to reagent layer 23 in probe 12. Alternatively, first protective film 51 in a paste form having a predetermined thickness is applied to the position including at least the part corresponding to reagent layer 23 in probe 12.

Here, the dipping for forming second protective film 52 is repeated a number of times from one to five, the immersing and the drying are preferably repeated any number of times from one to three, and the number of times may be any number of times as long as it is possible to cover the surface of probe 12 at the part corresponding to first protective film 51.

In this manner, the number of processes for forming the protective films of reagent layer 23 is reduced, and it is possible to easily manufacture sensor 1. Also, it is possible to reduce variations in thicknesses and shapes of the protective films and to reduce variations in performance by forming second protective film 52 that is thinner than first protective film 51 on first protective film 51 that is formed to be thick to some extent.

Hereinafter, terms and the like will be described. Parts overlapping the above description will also be included.

(Substrate)

Representative examples of the substrate include polyethylene terephthalate. However, the substrate is not particularly limited as long as it is a resin material or a plastic material with flexibility, easiness of working, and heat resistance. Other examples include polyethylene, polypropylene, and polyethylene terephthalate-based general-purpose plastic. Also, polyimide is preferably used in a case in which the substrate is required to have high heat resistance.

(Electrode)

An electrode material adopted for the working electrode and the counter electrode is not particularly limited as long as it is a metal or a carbon material with electrical conductivity and stability (it is unlikely to be oxidized or has salinity tolerance). Examples of such an electrode material include gold, platinum, palladium, and carbon. In a case in which a metal material is used, it is possible to form the electrode by sputtering, depositing, printing, plating, or spin-coating the electrode material on the substrate.

Also, in a case in which carbon is used, the electrode may be formed by screen printing using a carbon paste. In a case in which a configuration with the working electrode provided on the first surface and with the counter electrode provided on the second surface is adopted, the same electrode material may be used for the first surface and the second surface, or different electrode materials may be used.

As for the counter electrode, a plurality of counter electrodes may be provided in a case in which it is necessary to acquire electrical signals under a plurality of different conditions in order to improve accuracy of measurement results, for example. For example, both a first counter electrode (first counter electrode lead) and a second counter electrode (second counter electrode lead) may be provided on the first surface or the second surface, or a configuration in which the first counter electrode (first counter electrode lead) is provided on the first surface and the second counter electrode (second counter electrode lead) is provided on the second surface may be adopted.

(Reference Layer)

Ag/AgCl may be used for the reference layer. As a technique for forming Ag/AgCl as the reference layer, three techniques, namely a plating technique, a screen-printing technique, and an application technique are exemplified, and the application technique has been described above as an example.

(Insulating Layer)

The insulating layer is formed by a film or resist ink. A film that is formed of basically the same material as that of the substrate and includes an adhesive sheet (for example, an acrylic-based, rubber-based, or hot melt-based adhesive sheet) attached thereto is preferably used. However, the adhesive sheet may be used alone as the film.

Other examples include thermoplastic/photoplastic resist films. As the film, a general-purpose plastic film that is a material with a relationship "contact angle with film surface>contact angle with film opening in regard to the contact angle with the liquid is adopted in terms of application of the reagent. The film opening described herein indicates the surface of the working electrode before dropping and forming the reagent layer, that is, the first electrode material. Even if the material does not have such a contact angle, it is also possible to have the relationship of the contact angles by performing at least any of a water repellent treatment on the film surface and a hydrophilic treatment on the opening.

The film has a thickness selected from the range of equal to or greater than about 1 μm and equal to or less than 250 μm, preferably has a thickness of equal to or greater than 3 μm and equal to or less than 50 μm, and more preferably has a thickness of equal to or greater than 5 μm and equal to or less than 30 μm. For the insulating layer, it is more desirable to adopt the film as described in Embodiment 1 and Embodiment 2 than to form it with a resist ink.

(Reagent Layer)

The reagent layer contains oxidoreductase that causes an oxidation-reduction reaction with at least the analyte. In a case in which an oxidase-based enzyme is adopted in oxidoreductase, a configuration in which an electronic mediator is included in the reagent layer may be adopted, or a configuration in which the electronic mediator is not included (a system that detects generated hydrogen peroxide) may be adopted. On the other hand, in a case in which dehydrogenase-based enzyme is adopted, an electronic mediator is included in the reagent layer.

(Living Body Protective Film)

The living body protective film is adapted to prevent or reduce leakage of substances (mainly, oxidoreductase) contained in the reagent layer to the outside of the protective film and has a hole through which the analyte that is present outside the protective film can be transmitted to the inside of the protective film where the reagent layer is present. Therefore, the living body protective film is not particularly limited as long as it is a polymer with such a function.

Also, it is necessary for the living body protective film to be disposed to be able to cover at least the reagent layer. Moreover, since the probe of the sensor is used by being inserted into the living body, the living body protective film covering the surface thereof preferably has living body adaptability with which protein and cells are not adsorbed, or protein and cells are unlikely to be adsorbed, and in general, it is preferable to adopt a polymer having such a characteristic.

(Polymer)

As a polymer adopted for the living body protective film, either a polymer constituted by a single monomer or a copolymer constituted by two or more monomers may be used. As the copolymer, a copolymer constituted by any copolymerization, namely any of random copolymerization, alternating copolymerization, and block copolymerization may be adopted.

A polymer with a degree of polymerization of equal to or greater than 100 and with a molecular weight within a range of equal to or greater than 10,000 and equal to or less than 1,000,000 is preferably used, a polymer within a range of equal to or greater than 30,000 and equal to or less than 500,000 is more preferably used, and a polymer within a range of equal to or greater than 50,000 and equal to or less than 200,000 is yet more preferably used.

If the copolymer constituted of two monomers (a structural skeleton of one of the monomers will be referred to as a first structural skeleton, and a structural skeleton of the other monomer will be referred to as a second structural skeleton) is used, the ratio of the second structural skeleton in a case in which the ratio of the first structural skeleton is defined as 100 in regard to the ratios of the two structural skeletons preferably falls within a range of equal to or greater than 25 and equal to or less than 400, more preferably falls within a range of equal to or greater than 50 and equal to or less than 200, and yet more preferably falls within a range of equal to or greater than 75 and equal to or less than 150.

Also, if a copolymer constituted of three monomers (structural skeletons of the three monomers will be referred to as a first structural skeleton, a second structural skeleton, and a third structural skeleton) is used, both the ratios of the second structural skeleton and the third structural skeleton in a case in which the ratio of the first structural skeleton is defined as 100 in regard to the ratios of the three structural skeletons preferably fall within a range of equal to or greater than 1 and equal to or less than 400, more preferably fall within a range of equal to or greater than 3 and equal to or less than 100, and yet more preferably fall within a range of equal to or greater than 5 and equal to or less than 50.

The polymer (including not only the copolymer but also the polymer constituted of a single monomer) is preferably a polymer including a heterocyclic compound as the first structural skeleton, is more preferably a hetero atom-containing heterocyclic compound, and is further preferably a nitrogen-containing heterocyclic compound.

Examples of such a polymer other than the polymer including a nitrogen-containing heterocyclic compound as the first structural skeleton include polyurethane, a silicone-based polymer, polytetrafluoroethylene, polyethylene-co-tetrafluoroethylene, polypropylene, polyvinyl chloride, polyvinylidene fluoride, polybutylene terephthalate, polymethyl methacrylate, polyether ether ketone, polyurethane, a cellulose-based polymer, and polysulfone.

A specific example will be described using a polymer containing a nitrogen-containing heterocyclic compound as the first structural skeleton. Examples of the polymer constituted of a single monomer includes polyvinyl pyridines containing vinyl pyridines as a first structural skeleton and polyvinyl imidazoles containing vinyl imidazoles as the first structural skeleton. Specific compounds in the examples include poly(4-vinyl pyridine), poly(3-vinyl pyridine), and poly(2-vinyl pyridine) as the polyvinyl pyridines, and poly (l-vinyl imidazole), poly(2-vinyl imidazole), and poly(4-vinyl imidazole) as the vinyl imidazoles.

Examples of a copolymer constituted of the first and second structural skeletons from among the copolymers containing nitrogen-containing heterocyclic compounds include copolymers including styrenes or methacrylates as the second structural skeletons. Specific examples of the compound include poly(tert-butyl methacrylate-b-poly(4-vinyl pyridine).

Further, examples of a copolymer constituted of the first, second, and third structural skeletons from among the copolymers containing nitrogen-containing heterocyclic compounds include copolymers including styrenes (in a case in which the second structural skeleton is methacrylates) or methacrylates (in a case in which the second structural skeleton is styrenes) as the third structural skeleton. Specific examples of the compound include poly(styrene-co-4-vinyl pyridine-co-oligo[(propylene glycol methyl ether methacrylate)random].

Also, the polymers are preferably bound by covalent binding using a crosslinking agent in order to form the living body protective film using these polymers. This is because utilization of the crosslinking agent is considered to be useful to form a mesh as the living body protective film, prevent swelling of the living body protective film due to long-term utilization of the sensor, maintain the shape of the living body protective film, and to constantly maintain the permeability of glucose.

It is also possible to cause the crosslinking agent to have specific functions. In the example of tBuMA4VP that is the polymer adopted in this case, for example, PEGDGE (more specifically, PEGDGE1000) is adopted as the crosslinking agent. PEGDGE has a role in applying hydrophilicity to the living body protective film in addition to a role as the crosslinking agent.

Note that although the crosslinking agent to be adopted and the amount of addition thereof can be appropriately selected in accordance with the polymer to be adopted, the crosslinking agent is required to have a molecular structure having at least two glycidyl groups, and specific examples thereof include poly(ethylene glycol)diglycidyl ester and poly(propylene glycol)diglycidyl ester.

(Oxidoreductase)

When the analyte is glucose, for example, examples of oxidoreductase include glucose oxidase and glucose dehydrogenase. In regard to glucose dehydrogenase, it is desirable to employ FAD-bound glucose dehydrogenase in terms of low reactivity with respect to maltose, and for example, FAD-bound glucose dehydrogenase of the genus *Aspergillus* (*oryzae* or *terreus*) or the genus *Mucor* is preferably used.

(Electronic Mediator)

Examples of the electronic mediator include osmium complexes, ruthenium complexes, quinone compounds, phenazine compounds, ferrocene compounds, and derivatives thereof. In a case in which oxidase-based oxidoreductase is adopted, and the electronic mediator is not adopted, hydrogen peroxide generated in a reaction with glucose is detected.

Also, the electronic mediator may be configured to be bound with a polymer via a linker. The configuration is a preferable configuration for preventing and reducing leakage of the electronic mediator to the outside of the protective film (so-called the inside of the living body) to construct an embedded electrochemical sensor (having the protective film).

(Size (Width) of Probe)

It is desirable that the width of the probe fall within a range of equal to or greater than about 70 μm and equal to or less than 1700 μm in consideration of the embedding in the living body. The width is preferably equal to or greater than 70 μm and equal to or less than 600 μm and is more preferably equal to or greater than 70 μm and equal to or less than 400 μm.

Although the embodiments have been described with reference to the accompanying drawings, the present disclosure is not limited to such examples. It is obvious for those skilled in the art that various modification examples or amendment examples can be achieved within the scope described in the claims. It should be understood that such modification examples and amendment examples also belong to the technical scope of the present disclosure.

The components in the embodiments may be arbitrarily combined without departing from the gist of the present disclosure.

For example, trimmed portions may be formed in probe 12 described in Embodiment 2 similarly to probe 12 described in Embodiment 1.

A part of film 25 of probe 12 described in Embodiment 2 may overlap reagent layer 23 at both ends of reagent layer 23 in the insertion direction as described in FIG. 10. Also, film 25 on the side of the insertion direction may not be formed.

The present application claims benefits of priority from U.S. Provisional Application No. 62/983,013 filed on Feb. 28, 2020, the entirety of which is incorporated herein with reference to U.S. Provisional Application No. 62/983,013.

INDUSTRIAL APPLICABILITY

The present disclosure is suitable for use in a biosensor such as a CGM sensor, for example.

REFERENCE SIGNS LIST

1 Sensor
2 Living body
11 Main body
12 Probe
21 Substrate
22 Electrode
22*a* Working electrode
22*b* Reference electrode
22*c* Counter electrode
23 Reagent layer
24 Reference layer
25 Film
31 Upper surface
32 Back surface
33, 34 Side surface
35, 36 Trimmed portions
51 First protective film
52 Second protective film
61, 74 Protective film solution
62 Base material sheet
63 Squeegee
71 First film
72 Ethanol
73 Protective film sheet

The invention claimed is:

1. A sensor that measures an analyte, comprising:
a probe that is to be inserted into a living body,
wherein the probe includes
a substrate,
an electrode that is formed on or above the substrate,
a reagent layer that is formed on or above the electrode,
a first protective film that is formed on or above the reagent layer, and
a second protective film that is thinner than the first protective film and is formed on or above the first protective film,
wherein the first protective film has raised ends at opposite ends of the first protective film in an insertion direction of the probe into the living body.

2. The sensor according to claim 1, wherein the first protective film and the second protective film are formed in different processes.

3. The sensor according to claim 1, wherein the first protective film and the second protective film are made of the same material.

4. The sensor according to claim 1, wherein the first protective film and the second protective film include holes that transmit the analyte therethrough and do not transmit oxidoreductase contained in the reagent layer therethrough.

5. The sensor according to claim 1, wherein the first protective film is formed at a position separated from a distal end of the probe.

6. The sensor according to claim 5, wherein the second protective film is formed at least from the distal end of the probe to the first protective film.

7. The sensor according to claim 1, wherein the first protective film is also formed on or above a reference layer, the reference layer being formed on or above the electrode, wherein the reagent layer is arranged on a distal end side of the probe, and the reference layer is arranged on a side of the reagent layer that is opposite to the distal end side of the probe.

8. A method for manufacturing a sensor that includes a probe to be inserted into a living body and measures an analyte, the method comprising:
manufacturing the probe by
forming an electrode on or above a sheet-shaped substrate;
forming a reagent layer on or above the electrode;
forming a first protective film on or above the reagent layer;
cutting the sheet-shaped substrate into a shape of the probe;
immersing the substrate into a protective film solution and thereby forming a second protective film that is thinner than the first protective film on or above the first protective film;
after the forming of the reagent layer on or above the electrode, attaching a third film having a first opening with a size surrounding the reagent layer to the electrode such that the opening surrounds the reagent layer; and
dropping a first protective film solution obtained by dissolving a material of the first protective film onto the opening.

9. The method for manufacturing a sensor according to claim 8, wherein the first protective film has a sheet shape and is attached to the reagent layer.

10. The method for manufacturing a sensor according to claim 9, wherein before the sheet-shaped first protective film is attached to the reagent layer, a solution for dissolving the first protective film is dropped onto the reagent layer.

11. The method for manufacturing a sensor according to claim 8, wherein the third film has a second opening at a counter electrode part of the electrode.

12. The method for manufacturing a sensor according to claim 8, wherein the second protective film is formed by the immersing of the substrate into the protective film solution and drying, the immersing of the substrate and the drying being repeated any number of times from one to five.

* * * * *